US008552165B2

(12) United States Patent
Davis et al.

(10) Patent No.: US 8,552,165 B2
(45) Date of Patent: Oct. 8, 2013

(54) IMMUNOSTIMULATORY OLIGONUCLEOTIDES

(76) Inventors: Heather Davis, Donrobin (CA); Risini Weeratna, Ottawa (CA)

( * ) Notice: Subject to any disclaimer, the term of this patent is extended or adjusted under 35 U.S.C. 154(b) by 803 days.

(21) Appl. No.: 12/632,911

(22) Filed: Dec. 8, 2009

(65) Prior Publication Data
US 2010/0143400 A1 Jun. 10, 2010

Related U.S. Application Data

(60) Provisional application No. 61/121,022, filed on Dec. 9, 2008, provisional application No. 61/181,799, filed on May 28, 2009.

(51) Int. Cl.
*A61K 48/00* (2006.01)
*A61K 45/00* (2006.01)
*A61K 47/00* (2006.01)
*C07H 21/04* (2006.01)
*C07H 21/00* (2006.01)

(52) U.S. Cl.
USPC ...... 536/23.1; 536/25.3; 514/44 R; 424/278.1

(58) Field of Classification Search
None
See application file for complete search history.

(56) References Cited

U.S. PATENT DOCUMENTS

| | | | | |
|---|---|---|---|---|
| 4,469,863 | A | 9/1984 | Ts'o et al. | 536/23.1 |
| 5,023,243 | A | 6/1991 | Tullis | 514/44 |
| 5,658,738 | A | 8/1997 | Nadeau et al. | 435/6 |
| 5,668,265 | A | 9/1997 | Nadeau et al. | 536/23.1 |
| 6,124,806 | A * | 9/2000 | Cunningham et al. | 340/870.02 |
| 6,194,388 | B1 * | 2/2001 | Krieg et al. | 514/44 A |
| 6,207,646 | B1 * | 3/2001 | Krieg et al. | 514/44 R |
| 6,218,371 | B1 * | 4/2001 | Krieg et al. | 514/44 R |
| 6,239,116 | B1 * | 5/2001 | Krieg et al. | 514/44 A |
| 6,339,068 | B1 * | 1/2002 | Krieg et al. | 514/44 R |
| 6,406,705 | B1 * | 6/2002 | Davis et al. | 424/278.1 |
| 6,429,199 | B1 * | 8/2002 | Krieg et al. | 514/44 R |
| 6,821,957 | B2 * | 11/2004 | Krieg et al. | 514/44 R |
| 6,977,245 | B2 * | 12/2005 | Klinman et al. | 514/44 R |
| 7,223,741 | B2 * | 5/2007 | Krieg | 514/44 R |
| 7,271,156 | B2 * | 9/2007 | Krieg et al. | 514/44 A |
| 7,354,909 | B2 * | 4/2008 | Klinman et al. | 514/44 R |
| 7,402,572 | B2 * | 7/2008 | Krieg et al. | 514/44 R |
| 7,488,490 | B2 * | 2/2009 | Davis et al. | 424/278.1 |
| 7,514,414 | B2 * | 4/2009 | Klinman et al. | 514/44 R |
| 7,514,415 | B2 * | 4/2009 | Klinman et al. | 514/44 R |
| 7,517,861 | B2 * | 4/2009 | Krieg et al. | 514/44 R |
| 7,521,063 | B2 * | 4/2009 | Klinman et al. | 424/282.1 |
| 7,566,703 | B2 * | 7/2009 | Krieg et al. | 514/44 R |
| 7,569,553 | B2 * | 8/2009 | Krieg | 514/44 R |
| 7,605,138 | B2 * | 10/2009 | Krieg | 514/44 R |
| 7,615,227 | B2 * | 11/2009 | Klinman et al. | 424/198.1 |
| 7,615,539 | B2 * | 11/2009 | Uhlmann et al. | 514/44 R |
| 7,666,674 | B2 * | 2/2010 | Klinman et al. | 435/375 |
| 7,674,777 | B2 * | 3/2010 | Krieg et al. | 514/44 R |
| 7,713,529 | B2 * | 5/2010 | Krieg et al. | 424/184.1 |
| 7,723,022 | B2 * | 5/2010 | Krieg et al. | 435/5 |
| 7,723,500 | B2 * | 5/2010 | Krieg et al. | 536/23.1 |
| 7,758,876 | B2 * | 7/2010 | Klinman et al. | 424/278.1 |
| 7,776,344 | B2 * | 8/2010 | Hartmann et al. | 424/278.1 |
| 7,785,610 | B2 * | 8/2010 | Fearon et al. | 424/278.1 |
| 7,795,235 | B2 * | 9/2010 | Krieg et al. | 514/44 R |
| 7,807,803 | B2 * | 10/2010 | Krieg | 536/23.1 |
| 7,879,810 | B2 * | 2/2011 | Krieg et al. | 514/44 A |
| 7,884,083 | B2 * | 2/2011 | Van Nest et al. | 514/44 R |
| 7,888,327 | B2 * | 2/2011 | Krieg et al. | 514/44 R |
| 7,892,569 | B2 * | 2/2011 | Klinman et al. | 424/278.1 |
| 7,919,477 | B2 * | 4/2011 | Klinman et al. | 514/44 R |
| 7,935,351 | B2 * | 5/2011 | Klinman et al. | 424/198.1 |
| 7,935,675 | B1 * | 5/2011 | Krieg et al. | 514/44 R |
| 7,951,786 | B2 * | 5/2011 | Klinman et al. | 514/44 A |
| 7,956,043 | B2 * | 6/2011 | Krieg et al. | 514/44 R |
| 7,959,934 | B2 * | 6/2011 | Klinman et al. | 424/278.1 |
| 7,960,356 | B2 * | 6/2011 | Klinman et al. | 514/44 R |
| 7,993,648 | B2 * | 8/2011 | Kedl et al. | 424/153.1 |
| 7,993,659 | B2 * | 8/2011 | Noelle et al. | 424/278.1 |
| 7,998,492 | B2 * | 8/2011 | Ahluwalia et al. | 424/278.1 |
| 8,003,115 | B2 * | 8/2011 | Fearon et al. | 424/280.1 |
| 8,008,266 | B2 * | 8/2011 | Krieg et al. | 514/44 R |
| 8,017,749 | B2 * | 9/2011 | Das Gupta et al. | 536/23.1 |
| 8,021,834 | B2 * | 9/2011 | O'Hagan et al. | 435/5 |
| 8,027,834 | B2 * | 9/2011 | Hancock | 704/254 |
| 8,030,285 | B2 * | 10/2011 | Klinman et al. | 514/44 R |
| 8,034,802 | B2 * | 10/2011 | Averett | 514/183 |
| 8,043,622 | B2 * | 10/2011 | Klinman et al. | 424/184.1 |

(Continued)

FOREIGN PATENT DOCUMENTS

EP 092574 4/1983
WO 8301451 4/1983

(Continued)

OTHER PUBLICATIONS deVilliers et al, Vaccine, 2010, 28:2161-2168.*
Gupta et al, Drugs in R&D, 2008, 9/3:137-145.*
Samulowitz et al, Oligonucleotides, vol. 20, No. 2, 2010, pp. 93-101.*
Weeratna et al, Vaccine, 2005, 23:5263-5270.*
Luganini, A., et al., "Phosphorothioate-modified oligodeoxynucleotides inhibit human cytomegalovirus replication by blocking virus entry", Antimicrobial Agents and Chemotherapy, Mar. 2008, pp. 1111-1120, 52(3).
Vollmer, Jörg, et al., "Oligodeoxynucleotides lacking CpG dinucleotides mediate Toll-like receptor 9 dependent T helper type 2 biased immune stimulation", Immunology, Oct. 2004, pp. 212-223, 113(2).

(Continued)

*Primary Examiner* — Nita M Minnifield
(74) *Attorney, Agent, or Firm* — Keith D. Hutchinson; Matthew J. Pugmire

(57) ABSTRACT

The invention relates to immunostimulatory oligonucleotides and methods of using immunostimulatory oligonucleotides to induce an antigen-specific immune response. The invention further relates to a vaccine that comprises an immunostimulatory oligonucleotide and an antigen, and comprises a pharmaceutically acceptable carrier. The immunostimulatory oligonucleotides of the invention, in some embodiments, include one or more modified linkage(s).

4 Claims, 21 Drawing Sheets

(56) References Cited

U.S. PATENT DOCUMENTS

| | | | | |
|---|---|---|---|---|
| 8,053,422 | B2* | 11/2011 | Klinman et al. | 514/44 R |
| 8,058,249 | B2* | 11/2011 | Krieg et al. | 514/44 R |
| 8,114,418 | B2* | 2/2012 | Fearon et al. | 424/278.1 |
| 8,114,419 | B2* | 2/2012 | Krieg | 424/278.1 |
| 8,114,848 | B2* | 2/2012 | Krieg et al. | 514/44 R |
| 8,124,590 | B2* | 2/2012 | Van Nest et al. | 514/44 R |
| 8,129,351 | B2* | 3/2012 | Krieg et al. | 514/44 A |
| 8,158,592 | B2* | 4/2012 | Krieg et al. | 514/44 R |
| 8,188,254 | B2* | 5/2012 | Uhlmann et al. | 536/24.2 |
| 8,202,688 | B2* | 6/2012 | Davis et al. | 435/5 |
| 8,222,225 | B2* | 7/2012 | Klinman et al. | 514/44 R |
| 8,252,757 | B2* | 8/2012 | Hessel et al. | 514/44 R |
| 8,298,547 | B2* | 10/2012 | Brown et al. | 424/185.1 |
| 8,372,413 | B2* | 2/2013 | Fearon et al. | 424/278.1 |
| 2006/0229271 | A1 | 10/2006 | Krieg et al. | 514/44 |
| 2007/0129551 | A1* | 6/2007 | Ennifar | 546/279.1 |
| 2008/0131466 | A1* | 6/2008 | Reed et al. | 424/282.1 |
| 2008/0145375 | A1* | 6/2008 | Bembridge et al. | 424/184.1 |
| 2009/0017021 | A1* | 1/2009 | Davis et al. | 424/133.1 |
| 2009/0155307 | A1* | 6/2009 | Davis et al. | 424/204.1 |
| 2009/0181078 | A1* | 7/2009 | Reed et al. | 424/450 |
| 2009/0324641 | A1* | 12/2009 | Dominowski et al. | 424/207.1 |
| 2010/0143400 | A1* | 6/2010 | Davis et al. | 424/197.11 |
| 2010/0158933 | A1* | 6/2010 | Brown et al. | 424/185.1 |
| 2011/0052621 | A1* | 3/2011 | Champion et al. | 424/193.1 |
| 2011/0104210 | A1* | 5/2011 | Black et al. | 424/277.1 |
| 2011/0177109 | A1* | 7/2011 | Smith et al. | 424/185.1 |
| 2011/0217320 | A1* | 9/2011 | Ennifar et al. | 424/175.1 |
| 2011/0300163 | A1* | 12/2011 | Champion et al. | 424/183.1 |
| 2011/0300174 | A1* | 12/2011 | Brown et al. | 424/194.1 |
| 2012/0052088 | A1* | 3/2012 | Davis et al. | 424/197.11 |
| 2013/0084306 | A1* | 4/2013 | Davis et al. | 424/196.11 |

FOREIGN PATENT DOCUMENTS

| | | | |
|---|---|---|---|
| WO | 9602555 | | 2/1996 |
| WO | 9818810 | | 5/1998 |
| WO | WO 2005/025614 | * | 3/2005 |
| WO | WO 2006/071934 | * | 7/2006 |
| WO | WO 2010/067286 A2 | * | 6/2010 |
| WO | WO 2010/125480 | * | 11/2010 |
| WO | WO 2011/013034 A1 | * | 2/2011 |
| WO | WO 2011/052621 A1 | * | 3/2011 |
| WO | WO 2011/148356 A1 | * | 12/2011 |

OTHER PUBLICATIONS

PCT International Search Report and Written Opinion for PCT/IB2009/055444, dated Mar. 22, 2010; 8 pages.

Tokunaga, T., et al., "A Synthetic Single-Stranded DNA, Poly (dG,dC), Induces Interferon-α/β and -γ, Augments Natural Killer Activity, and Suppresses Tumor Growth", Japan Journal of Cancer Research, Jun. 1988, pp. 682-686, vol. 79.

Tokunaga, T., et al., "Antitumor Activity of Deoxyribonucleic Acid Fraction From Mycobacterium bovis BCG. I. Isolation, Physicochemical Characterization, and Antitumor Activity[1,2]", JNCI, Apr. 1984, pp. 955-962, vol. 72, No. 4.

Messina, J., et al., "Stimulation of In Vitro Murine Lymphocyte Proliferation by Bacterial DNA[1]", Journal of Immunology, Sep. 15, 1991, pp. 1759-1764, vol. 147, No. 6.

Krieg, Arthur M., "Leukocyte Stimulation by Oligodeoxynucleotides", In: Applied Antisense Oligonucleotide Technology, 1998, pp. 431-448, Chapter 24.

Krieg, A. M., et al., "CpG motifs in bacterial DNA trigger direct B-cell activation", Nature, Apr. 6, 1995, pp. 546-549, vol. 374.

Krieg, A.M., et al., "Mechanisms and applications of immune stimulatory CpG oligodeoxynucleotides", Biochimics et Biophysica Acta, 1999, pp. 107-116, vol. 1489.

Ballas, Z.K., et al., "Induction on NK Activity in Murine and Human Cells by CpG Motifs in Oligodeoxynucleotides and Bacterial DNA[1]" Journal of Immunology, Sep. 1, 1996, pp. 1840-1845, vol. 157, No. 5.

Hartman, G., et al., "Delineation of a CpG Phosphorothioate Oligodeoxynucleotide for Activating Primate Immune Responses In Vitro and In Vivo[1]" Journal of Immunology, 2000, pp. 1617-1624, vol. 164, No. 3.

Klinman, D.M., et al., "Hierarchical Recognition of CpG Motifs Expressed by Immunostimulatory Oligodeoxynucleotides" Clinical & Experimental Immunology, 2003, pp. 227-232, vol. 133, No. 2.

Hartmann, G., et al., "CpG DNA: A potent signal for growth, activation, and maturation of human dendritic cells", Proceeding of National Academy of Sciences of the United States of America, Aug. 3, 1999, pp. 9305-9310, vol. 96.

Uhlmann, E., et al., "Antisense Oligonucleotides: A New Therapeutic Principle", Chemical Reviews, Jun. 1990, pp. 543-584, vol. 90, No. 4.

Crooke, S.T., et al., "Progress in Antisense Oligonucleotide Therapeutics" Annual Review of Pharmacology and Toxicology, Apr. 1996, pp. 107-129, vol. 36.

Hunziker, J., et al., "Nucleic Acid Analogues: Synthesis and Properties", Modern Synthesis Methods, 1995, pp. 331-417, vol. 7.

Wagner, R.W., et al., "Potent and selective inhibition of gene expression by an antisense heptanucleotide", Nature Biotechnology, Jul. 1996, pp. 840-844, vol. 14, No. 7.

Goodchild, John, "Conjugates of Oligonucleotides and Modified Oligonucleotides: A Review of Their Synthesis and Properties", Bioconjugate Chemistry, May/Jun. 1990, pp. 165-187, vol. 1, No. 3.

Seliger, H., et al., "Oligonucleotide Analogues with Terminal 3'-3' and 5'-5'-Internucleotidic Linkages As Antisense Inhibtors of Viral Gene Expression", Nucleosides & Nucleotides, 1991, pp. 469-477, vol. 10, No. 1-3.

Jiang, Z., et al., "Pseudo-Cyclic Oligonucleotides: In Vitro and In Vivo Properties", Bioorganic & Medicinal Chemistry, Dec. 1999, pp. 2727-2735, vol. 7, No. 12.

Durand, M., et al., "Triple-Helix Formation by an Oligonucleotide Containing One $(dA)_{12}$ and Two $(dT)_{12}$ Sequences Bridged by Two Hexaethylene Glycol Chains", Biochemistry, Sep. 1992, pp. 9197-9204, vol. 31, No. 38.

Fontanel, Marie-Laurence, et al., "Sterical recognition by $T_4$ polynucleotide kinase of non-nucleosidic moieties 5'-attached to oligonucleotides", Nucleic Acids Research, 1994, pp. 2022-2027, vol. 22, No. 11.

Uhlmann, E. et al., "Oligonucleotide Analogs Containing Dephospho-Internucleoside Linkages", Methods in Molecular Biology, 1993, pp. 355-389, Chapter 16, vol. 20.

Stirchak, E.P., et al., "Uncharged stereoregular nucleic acid analogs: 2. Morpholino nucleoside oligomers with carbamate internucleoside linkages", Nucleic Acids Research, Jun. 1989, pp. 6129-6141, vol. 17, No. 15.

Nielsen, P.E., et al., "Peptide Nucleic Acid (PNA). A DNA Mimic with a Peptide Backbone", Bioconjugate Chemistry, Jan. 1994, pp. 3-7-, vol. 5, No. 1.

Froehler, B., et al., "Triple-Helix Formation by Oligodeoxynucleotides Containing the Carbocyclic Analogs of Thymidine and 5-Methyl-2'-deoxycytidine", Journal American Chemical Society, 1992, pp. 8320-8322, vol. 114.

Vandendriessche, F., et al., "Acyclic Oligonucleotides: Possibilities and Limitations", Tetrahedron, Aug. 20, 1993, pp. 7223-7238, vol. 49, No. 33.

Tarköy, M., et al., Nucleic-Acid Analogues with Constraint Conformational Flexibility in the Sugar-Phosphate Backbone ('Bicyclo-DNA'), Helvetica Chimica Acta, 1993, pp. 481-510, vol. 76, No. 1.

Beaucage, S.L., et al., "Deoxynucleoside Phosphoramidites—A New Class of Key Intermediates for Deoxypolynucleotide Synthesis", Tetrahedron Letters, 1981, pp. 1859-1862, vol. 22, No. 20.

Garegg, P.J., et al., "Nucleoside H-Phosphonates. III. Chemical Synthesis of Oligodeoxyribonucleotides by the Hydrogenphosphonate Approach", Tetrahedron Letters, 1986, pp. 4051-4054, vol. 27, No. 34.

Froehler, B.C., et al., "Synthesis of DNA via deoxynucleoside H-phosphonate intermediates" Nucleic Acids Research, Jul. 11, 1986, pp. 5399-5407, vol. 14, No. 13.

Garegg, P.J., et al., "Nucleoside H-Phosphonates. IV. Automated Solid Phase Synthesis of Oligoribonucleotides by the Hydrogenphosphonate Approach", Tetrahedron Letters, 1986, pp. 4055-4058, vol. 27, No. 34.

Gaffney, B. L., et al., "Large-Scale Oligonucleotide Synthesis by the H-Phosphonate Method", Tetrahedron Letters, 1988, pp. 2619-2622, vol. 29, No. 22.

(56) References Cited

OTHER PUBLICATIONS

Langer R., "New Methods of Drug Delivery", Science, Sep. 28, 1990, pp. 1527-1533, vol. 249.
Abuchowski, A., et al., "Soluble Polymer-Enzyme Adducts", Enzymes as Drugs, 1981, Chapter 13, pp. 367-383, Hocenberg and Roberts, eds., Wiley-Interscience publication, John Wiley & Sons Inc., New York, New York.
Ortigao, J.F.R et al., "Antisense Effect of Oligodeoxynucleotides with Inverted Terminal Internucleotidic Linkages: A Minimal Modification Protecting Against Nucleolytic Degradation", Antisense Research and Development, 1992, pp. 129-146, vol. 2.
Newmark, et al., "Preparation and Properties of Adducts of Streptokinase and Streptokinase-Plasmin Complex with Polyethylene Glycol and Pluronic Polyol F38", Journal of Applied Biochemistry, 1982, pp. 185-189, vol. 4.
Harari, A., et al., "Functional Signatures of Protective Antiviral T-Cell Immunity in Human Virus Infections", Immunological Reviews, Jun. 2006, pp. 236-254, vol. 211, No. 1.
Precopio, M.L., et al., "Immunization with Vaccinia Virus Induces Polyfunctional and Phenotypically Distinctive $CD8^+T$ Cell Responses", Journal of Experimental Medicine, Jun. 11, 2007, pp. 1405-1416, vol. 204, No. 6.
Xu, R., et al., "Comparative Ability of Various Plasmid-based Cytokines and Chemokines to Adjuvant the Activity of HIV Plasmid DNA Vaccines", Vaccines, Sep. 2, 2008, pp. 4819-4829, vol. 26, No. 37.
Makedonas, G., et al., "Polyfunctional Analysis of Human T Cell Responses: Importance in Vaccine Immunogenicity and Natural Infection", Springer Seminars Immunopathology, 2006, pp. 209-219, vol. 28, No. 3.
WO 83/01451 equivalent to EP092574.

\* cited by examiner

| ODN | IFN-α (6 donors) | | MCP-1 (3 donors) | | IP-10 (6 donors) | |
| --- | --- | --- | --- | --- | --- | --- |
| | EC50 (nM) | Max (pg/mL) | EC50 (nM) | Max (pg/mL) | EC50 (nM) | Max (pg/mL) |
| CPG 10103 | 410 | 640 | 460 | 13,850 | 570 | 520 |
| CpG 24555 | 310 | 800 | 390 | 17,990 | 220 | 490 |
| Non-CpG ODN 22881 | 1,570 | 200 | 1,170 | 640 | 330 | 100 |

Figure 9A.

| ODN | IL-6 (5 donors) | | IL-10 (6 donors) | | IL-2R (3 donors) | |
| --- | --- | --- | --- | --- | --- | --- |
| | EC50 (nM) | Max (pg/mL) | EC50 (nM) | Max (pg/mL) | EC50 (nM) | Max (pg/mL) |
| CPG 10103 | 120 | 330 | 120 | 120 | 390 | 170 |
| CpG 24555 | 190 | 450 | 100 | 160 | 190 | 200 |
| Non-CpG ODN 22881 | 210 | 210 | 140 | 20 | 250 | 140 |

Figure 9B.

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
tcgtcgtttt tcggtgcttt t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
tcgtcgtttt tcggtcgttt t                                              21

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
tcgtcgtttt gtcgttttgt cgtt                                           24

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
tgctgctttt tggctgcttt t                                              21

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 5
tgctgctttt gtgcttttgt gctt                                            24
```

IMMUNOSTIMULATORY OLIGONUCLEOTIDES

RELATED APPLICATIONS

This application claims priority under 35 U.S.C. §119(e) to U.S. Provisional Application No. 61/121,022, filed Dec. 9, 2008 and U.S. Provisional Application No. 61/181,799, filed May 8, 2009, and claims priority to International Application No. PCT/IB2009/055444, filed Dec. 1, 2009, the entire contents of which are hereby incorporated by reference.

FIELD OF THE INVENTION

The invention relates to immunostimulatory oligonucleotides and methods of using immunostimulatory oligonucleotides to induce an antigen-specific immune response.

BACKGROUND OF THE INVENTION

Bacterial DNA has immune stimulatory effects to activate B cells and natural killer cells, but vertebrate DNA does not (Tokunaga, T., et al., 1988. Jpn. J. Cancer Res. 79:682-686; Tokunaga, T., et al., 1984, JNCI 72:955-962; Messina, J. P., et al., 1991, J. Immunol. 147:1759-1764; and reviewed in Krieg, 1998, In: Applied Oligonucleotide Technology, C. A. Stein and A. M. Krieg, (Eds.), John Wiley and Sons, Inc., New York, N.Y., pp. 431-448). It is now understood that these immune stimulatory effects of bacterial DNA are a result of the presence of unmethylated CpG dinucleotides in particular base contexts (CpG motifs), which are common in bacterial DNA, but methylated and underrepresented in vertebrate DNA (Krieg et al, 1995 Nature 374:546-549; Krieg, 1999 Biochim. Biophys. Acta 1489:107-116). The immune stimulatory effects of bacterial DNA can be mimicked with synthetic oligodeoxynucleotides (ODN) containing these CpG motifs. Such CpG ODN have highly stimulatory effects on human and murine leukocytes, inducing B cell proliferation; cytokine and immunoglobulin secretion; natural killer (NK) cell lytic activity and IFN-.gamma. secretion; and activation of dendritic cells (DCs) and other antigen presenting cells to express costimulatory molecules and secrete cytokines, especially the Th1-like cytokines that are important in promoting the development of Th1-like T cell responses. These immune stimulatory effects of native phosphodiester backbone CpG ODN are highly CpG specific in that the effects are dramatically reduced if the CpG motif is methylated, changed to a GpC, or otherwise eliminated or altered (Krieg et al, 1995 Nature 374:546-549; Hartmann et al, 1999 Proc. Natl. Acad. Sci. USA 96:9305-10).

It has been previously reported that immunostimulatory activity of CpG oligonucleotides is dependent on the number of CpG motifs, the sequences flanking the CG dinucleotide, the location of the CpG motif(s) and the spacing between the CpG motifs (Ballas et al., 1996, J. Immunol. 157(5): 1840-5; Hartmann et al., 2000, J. Immunol., 164(3): 1617-24; Klinman et al., 2003, Clin. Exp. Immunol., 133(2): 227-32). An immunostimulatory oligonucleotide having the 3' CpG motif removed is disclosed herein that surprisingly retains its immunostimulatory activity. A vaccine comprising the immunostimulatory oligonucleotide and an antigen, and methods of using such vaccine are further disclosed.

BRIEF SUMMARY OF THE INVENTION

In aspects of the invention, an immunostimulatory oligonucleotide comprising the nucleotide sequence 5' TCGTCGTTTTTCGGTGCTTTT 3' (SEQ ID NO:1) is provided. In some embodiments, the immunostimulatory oligonucleotide comprises one or more modified linkages. In certain embodiments, the immunostimulatory oligonucleotide comprises one or more phosphorothioate linkages. In certain embodiments, all internucleotide linkages of the oligonucleotide are phosphorothioate linkages. In some embodiments, the immunostimulatory oligonucleotide comprises at least one lipophilic substituted nucleotide analog and a pyrimidine-purine dinucleotide.

In aspects of the invention, a vaccine comprising an antigen and an immunostimulatory oligonucleotide comprising the nucleotide sequence SEQ ID NO:1, further comprising a pharmaceutically acceptable carrier is provided. In some embodiments, the immunostimulatory oligonucleotide is in an effective amount to induce an antigen-specific immune response. In other embodiments, the antigen-specific immune response induced is a Th1 immune response. In some embodiments, the antigen is a microbial antigen, a self antigen or an addictive substance. In other embodiments, the bacterial antigen is associated with *Staphylococcus aureus*, or the bacterial antigen is associated with a bacterium that causes dental caries. In further embodiments, the bacterium is *Streptococcus mutans, Streptococcus sobrinus, Streptococcus sanguis, Lactobacillus acidophilis*, or *Actinomyces viscosus*. In other embodiments, the bacterial antigen is associated with a bacterium that causes periodontal disease. In further embodiments, the bacterium is *Porphyromonas gingivalis* or *Actinobacillus actinomycetemcomitans*. In some embodiments, the viral antigen is associated with Respiratory Syncytial virus (RSV), Herpes Simplex virus 1, Herpes Simplex virus 2, Human Immunodeficiency Virus-1 (HIV-1) or HIV-2. In other embodiments, the parasitic antigen is associated with a parasite that causes malaria. In some embodiments, the self antigen is a tumor antigen, an antigen associated with Alzheimer's Disease, an antigen against a human antibody, or an antigen that is expressed from human endogenous retroviral elements. In further embodiments, the tumor antigen is HER2, MAGE, NY-ESO, PSA, CEA or a variant form of EGFR. In other embodiments, wherein the antigen is associated with Alzheimer's Disease, the antigen is tau or β-amyloid. In some embodiments, the antigen is IgE. In some embodiments, the antigen is a nicotine hapten conjugated to a carrier. In further embodiments, the carrier to which the nicotine hapten is conjugated is diphtheria toxin (DT). In other embodiments, the antigen is a peptide, a recombinant protein, a purified protein, whole killed pathogen, live attenuated virus or viral vector, live attenuated bacteria or a bacterial vector, a polysaccharide, a hapten, or encoded by plasmid DNA.

In some embodiments, the antigen is conjugated to a carrier. In further embodiments, the carrier is diphtheria toxin (DT). In other embodiments, the carrier is a virus-like particle. In further embodiments, the virus-like particle is RNA phage Q-β, hepatitis B surface antigen (HBsAg), or hepatitis B core antigen (HBcAg). In some embodiments, the vaccine further comprises one or more adjuvants. In further embodiments, the adjuvant is an agonist for a Toll-like receptor (TLR) that is not TLR 9. In other embodiments, the agonist is for TLR 3. In further embodiments, the TLR 3 agonist is stabilized polyI:C. In some embodiments, the agonist is for TLR 4. In further embodiments, the TLR 4 agonist is a derivative of lipopolysaccharide (LPS). In even further embodiments, the LPS derivative is MPL or GLA. In other embodiments, the agonist is for TLR 5. In further embodiments, the TLR 5 agonist is flagellin. In some embodiments, the agonist is for TLR 7 or 8. In further embodiments, the TLR 7 or 8 agonist is a small molecule of the imidazoquinoline family. In other embodiments, the adjuvant is an aluminum salt. In further embodiments, the aluminum salt is aluminum hydroxide. In some embodiments, the adjuvant is an immune stimulatory complex (ISCOM). In other embodiments, the adjuvant is an oil-in-water or water-in-oil emulsion. In some embodiments, the adjuvant is a liposome. In other embodiments, the adjuvant is a delivery system. In further embodiments, the delivery system is a nanoparticle or a microparticle.

In some embodiments, the immunostimulatory oligonucleotide comprises one or more modified linkages. In further embodiments, the immunostimulatory oligonucleotide comprises one or more phosphorothioate linkages. In certain embodiments, all internucleotide linkages of the oligonucleotide are phosphorothioate linkages. In other embodiments, the immunostimulatory oligonucleotide comprises at least one lipophilic substituted nucleotide analog and a pyrimidine-purine dinucleotide. In some embodiments, the vaccine is formulated for administration. In further embodiments, the vaccine is formulated for administration via a parenteral route, wherein the parental route is intramuscular, subcutaneous, intradermal, intravenous or intraperitoneal. In still further embodiments, the vaccine is formulated for administration via a topical route, wherein the topical route is the skin, transdermal or a mucosal surface. In further embodiments, the mucosal route is oral, intranasal, intravaginal, intrarectal, intra-buccal or intraocular.

In some aspects of the invention, a method of inducing an antigen-specific immune response in a subject in need thereof comprises administering to a subject an antigen and an immunostimulatory oligonucleotide comprising nucleotide sequence SEQ ID NO:1 in an effective amount to induce an antigen-specific immune response in said subject. In some embodiments, the antigen is a microbial antigen, a self antigen or an addictive substance. In further embodiments, the microbial antigen is a bacterial antigen, a viral antigen or a parasitic antigen. In other embodiments, the bacterial antigen is associated with *Staphylococcus aureus*, or the bacterial antigen is associated with a bacterium that causes dental caries. In further embodiments, the bacterium is *Streptococcus mutans, Streptococcus sobrinus, Streptococcus sanguis, Lactobacillus acidophilis*, or *Actinomyces viscosus*. In other embodiments, the bacterial antigen is associated with a bacterium that causes periodontal disease. In further embodiments, the bacterium is *Porphyromonas gingivalis* or *Actinobacillus actinomycetemcomitans*. In some embodiments, the viral antigen is associated with Respiratory Syncytial virus (RSV), Herpes Simplex virus 1, Herpes Simplex virus 2, Human Immunodeficiency Virus-1 (HIV-1) or HIV-2. In other embodiments, the parasitic antigen is associated with a parasite that causes malaria. In some embodiments, the self antigen is a tumor antigen, an antigen associated with Alzheimer's Disease, an antigen against a human antibody, or an antigen that is expressed from human endogenous retroviral elements. In further embodiments, the tumor antigen is HER2, MAGE, NY-ESO, PSA, CEA or a variant form of EGFR. In other embodiments, wherein the antigen is associated with Alzheimer's Disease, the antigen is tau or β-amyloid. In some embodiments, the antigen is IgE. In some embodiments, the antigen is a nicotine hapten conjugated to a carrier. In further embodiments, the carrier to which the nicotine hapten is conjugated is diphtheria toxin (DT). In other embodiments, the antigen is a peptide, a recombinant protein, a purified protein, whole killed pathogen, live attenuated virus or viral vector, live attenuated bacteria or a bacterial vector, a polysaccharide, a hapten, or encoded by plasmid DNA.

In some embodiments, the antigen is conjugated to a carrier. In further embodiments, the carrier is diphtheria toxin (DT). In other embodiments, carrier is a virus-like particle. In further embodiments, the virus-like particle is RNA phage Q-6, hepatitis B surface antigen (HBsAg), or hepatitis B core antigen (HBcAg). In some embodiments, the vaccine further comprises one or more adjuvants. In further embodiments, the adjuvant is an agonist for a Toll-like receptor (TLR) that is not TLR 9. In other embodiments, the agonist is for TLR 3. In further embodiments, the TLR 3 agonist is stabilized polyI:C. In some embodiments, the agonist is for TLR 4. In further embodiments, the TLR 4 agonist is a derivative of lipopolysaccharide (LPS). In even further embodiments, the LPS derivative is MPL or GLA. In other embodiments, the agonist is for TLR 5. In further embodiments, the TLR 5 agonist is flagellin. In some embodiments, the agonist is for TLR 7 or 8. In further embodiments, the TLR 7 or 8 agonist is a small molecule of the imidazoquinoline family. In other embodiments, the adjuvant is an aluminum salt. In further embodiments, the aluminum salt is aluminum hydroxide. In some embodiments, the adjuvant is an immune stimulatory complex (ISCOM). In other embodiments, the adjuvant is an oil-in-water or water-in-oil emulsion. In some embodiments, the adjuvant is a liposome. In other embodiments, the adjuvant is a delivery system. In further embodiments, the delivery system is a nanoparticle or a microparticle.

In some embodiments, the immunostimulatory oligonucleotide comprises one or more modified linkages. In further embodiments, the immunostimulatory oligonucleotide comprises one or more phosphorothioate linkages. In certain embodiments, all internucleotide linkages of the oligonucleotide are phosphorothioate linkages. In other embodiments, the immunostimulatory oligonucleotide comprises at least one lipophilic substituted nucleotide analog and a pyrimidine-purine dinucleotide. In some embodiments, the antigen and/or immunostimulatory oligonucleotide is formulated for administration. In further embodiments, the antigen and/or immunostimulatory oligonucleotide are/is formulated for administration via a parenteral route, wherein the parental route is intramuscular, subcutaneous, intradermal, intravenous or intraperitoneal. In still further embodiments, the antigen and/or immunostimulatory oligonucleotide are/is formulated for administration via a topical route, wherein the topical route is the skin, transdermal or a mucosal surface. In further embodiments, the mucosal route is oral, intranasal, intravaginal, intrarectal, intra-buccal or intraocular. In some embodiments, the antigen and immunostimulatory oligonucleotide are administered via the same, similar or different routes. In other embodiments, the antigen and immunostimulatory oligonucleotide are administered in conjunction, simultaneously or separately. In further embodiments, the antigen and immunostimulatory oligonucleotide are administered within 24 hours of each other. In some embodiments, the subject is a species treated by veterinarian medicine. In other embodiments, the subject is a non-rodent subject. In some embodiments, the subject is a human.

with OVA only. Plasma from 2 weeks (for HBsAg) or 1 week (for OVA) post last boost was assayed for antigen-specific total IgG, IgG1 and IgG2a/c levels (anti-HBs or anti-OVA). Each bar represents the geometric mean (±SEM) titres for total IgG. Titers were defined as the highest dilution resulting in an absorbance value two times that of non-immune plasma with a cut-off value of 0.05. The numbers above each bar represents the ratio of antigen specific IgG2a (or 2c)/IgG1.

Figure 2:
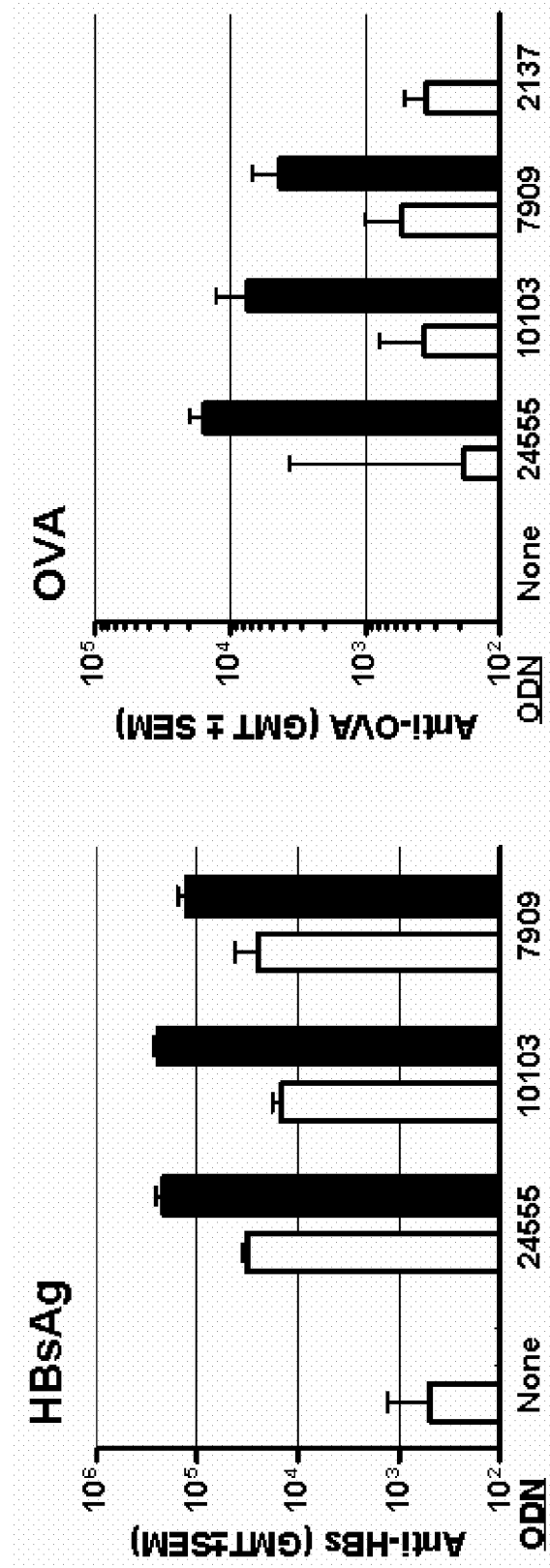

FIG. 2: Nature of the humoral immune response induced in mice. Adult (6-8 wk; n=10/gp) mice were immunized with 1 μg of HBsAg (left hand panel) or 20 μg OVA (right hand panel) without adjuvant or in combination with CPG 24555, 10103 or 7909 (10 μg) or non-CpG control ODN 2137 (10 μg; with OVA only). Plasma from 2 weeks (for HBsAg) or 1 week (for OVA) post last boost was assayed for IgG1 (clear bars) and IgG2a or IgG2c (black bars) levels against HBsAg (Anti-HBs) or OVA (anti-OVA). Each bar represents the geometric mean (±SEM) of the ELISA end point dilution titer for the entire group (n=10). Titers were defined as the highest dilution resulting in an absorbance value two times that of non-immune plasma with a cut-off value of 0.05.

Figure 3:
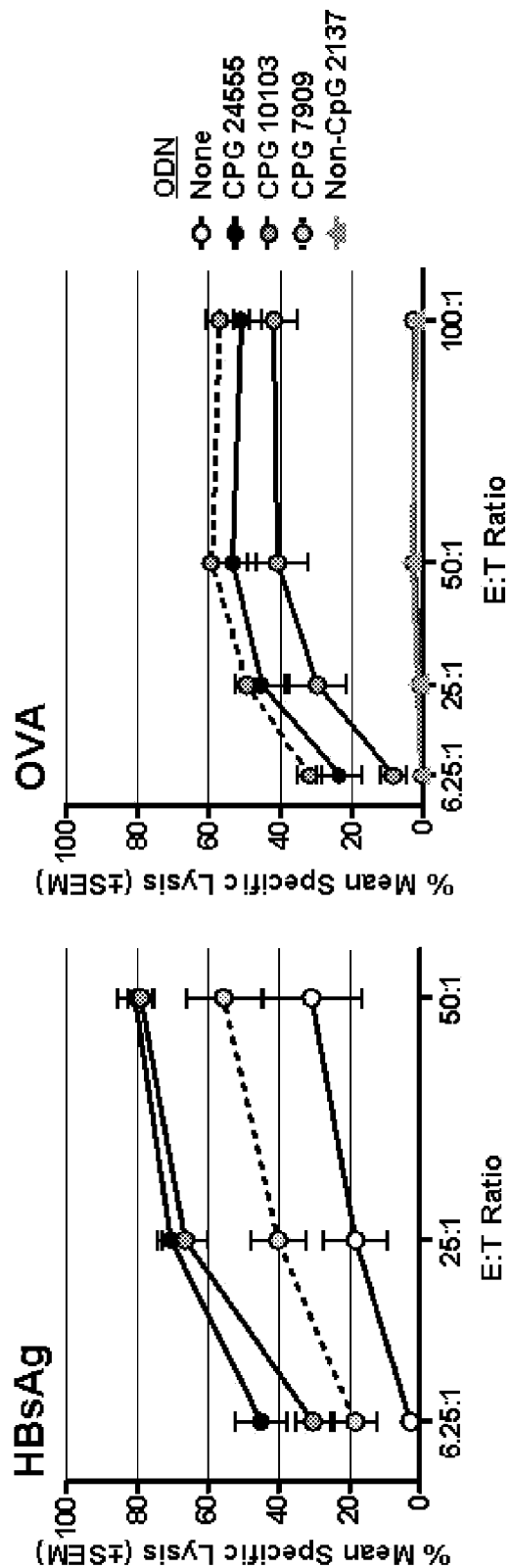

FIG. 3: Cytotoxic T lymphocyte responses induced in mice. Adult (6-8 wk; n=5/gp) mice were immunized with 1 μg of HBsAg (left hand panel) or 20 μg OVA (right hand panel) without adjuvant or in combination with CPG 24555, 10103 or 7909 (10 μg) or non-CpG control ODN 2137 (10 μg; with OVA only). Splenocytes from 2 weeks (for HBsAg) or 1 week (for OVA) post last boost was assayed for antigen specific CTL responses using standard $^{51}$Cr release assay.

Figure 4:
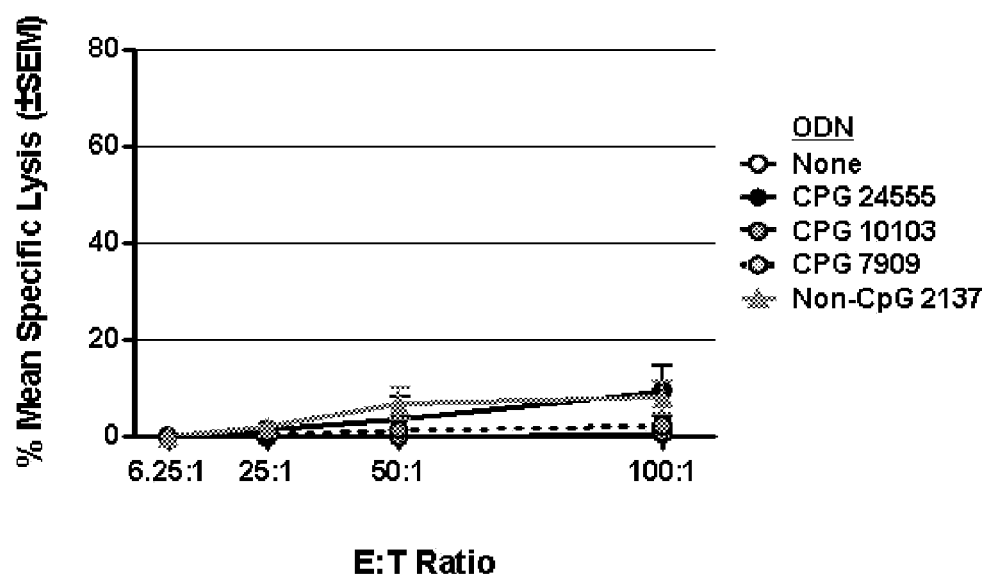

FIG. 4: No CpG mediated augmentation in CTL responses in TLR9 deficient mice. TLR9 deficient adult (6-8 wk; n=5 gp) mice were immunized with 20 μg OVA without adjuvant or in combination with CPG 24555, 10103 or 7909 (10 μg) or non-CpG control ODN 2137 (10 μg). Splenocytes from 1 week post last boost was assayed for OVA specific CTL responses using standard $^{51}$Cr release assay.

Figure 5:
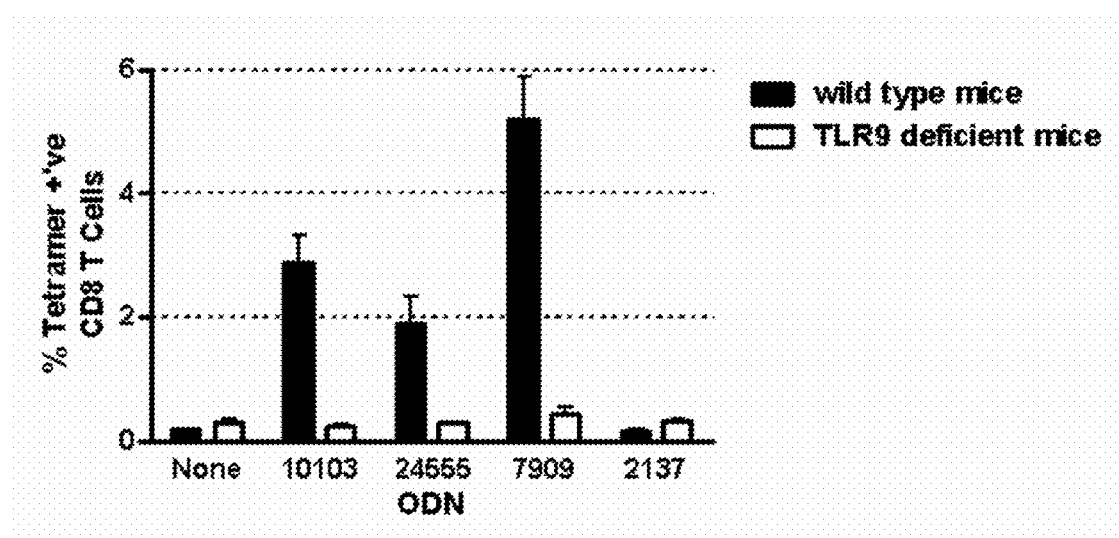

FIG. 5: OVA specific CD8 T cells in wild type vs. TLR9 deficient mice. Wild type and TLR9 deficient adult (6-8 wk; n=5/gp) mice were immunized with 20 μg OVA without adjuvant or in combination with CPG 24555, 10103 or 7909 (10 μg) or non-CpG control ODN 2137 (10 μg). Splenocytes from 1 week post last boost were assayed for OVA specific CD8 T cells using MHC Class I H-2 Kb-SIINFEKL tetramers.

Figure 6:
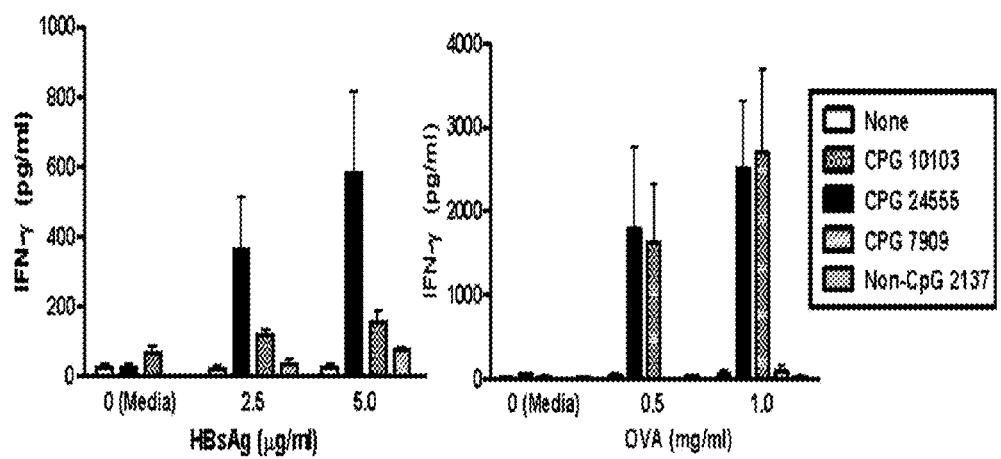

FIG. 6: Antigen specific IFN-g secretion in mice. Adult (6-8 wk; n=5/gp) mice were immunized with 1 μg of HBsAg (left hand panel) or 20 μg OVA (right hand panel) without adjuvant or in combination with CPG 24555, 10103 or 7909 (10 μg) or non-CpG control ODN 2137 (10 μg; with OVA only). Splenocytes from 2 weeks (for HBsAg) or 1 week (for OVA) post last boost were stimulated with the relevant antigen as shown in the figures for 72 hr and culture supernatants assayed for IFN-γ by ELISA.

Figure 7:
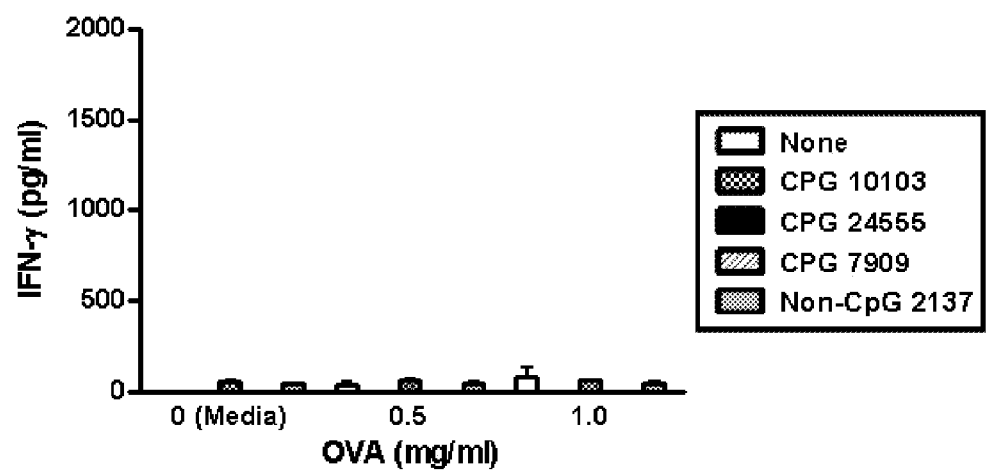

FIG. 7: No CpG mediated augmentation in antigen specific IFN-g secretion in TLR9 deficient mice. TLR9 deficient adult (6-8 wk; n=5/gp) mice were immunized with 20 μg OVA without adjuvant or in combination with CPG 24555, 10103 or 7909 (10 μg) or non-CpG control ODN 2137 (10 μg). Splenocytes 1 week post last boost were stimulated with OVA at 0, 0.5 and 1 mg/ml concentrations for 72 hr and culture supernatants assayed for IFN-γ by ELISA.

Figure 8:
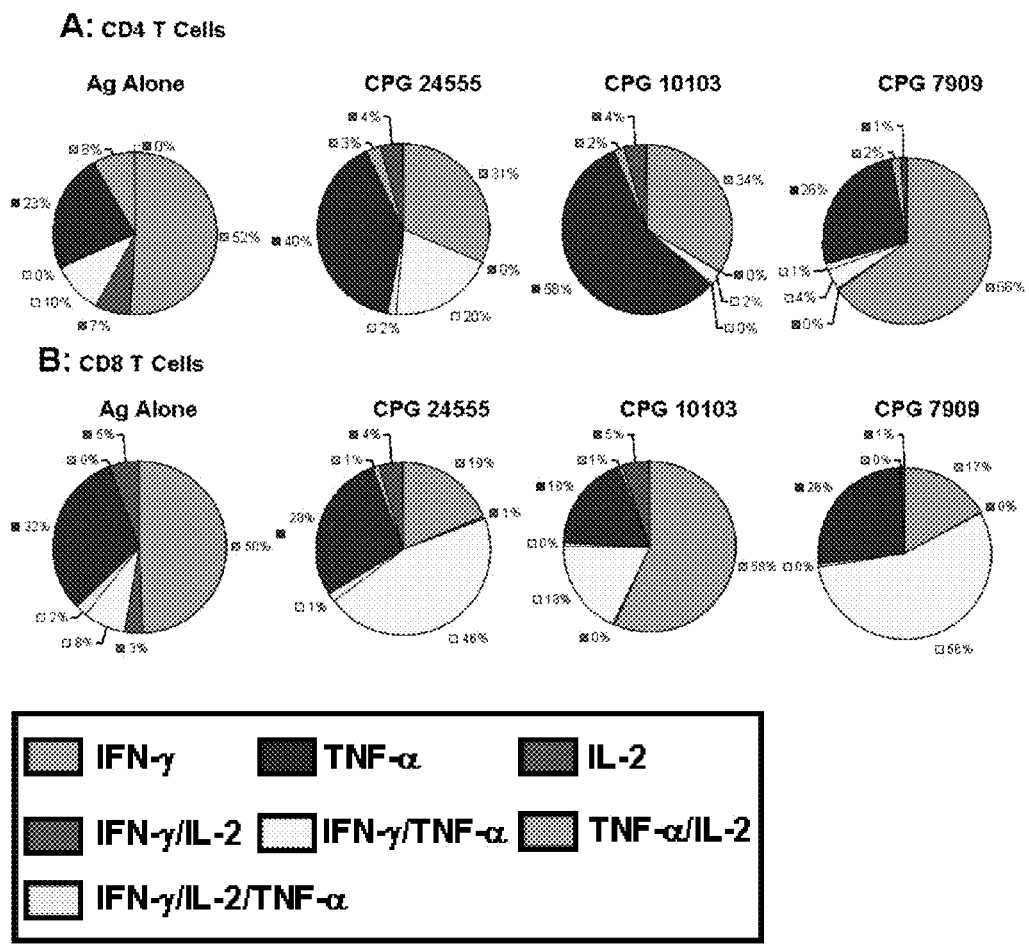

FIG. 8: Antigen specific multi-cytokine secreting T cell populations in mice. Adult (6-8 wk; n=5/gp) mice were immunized with 1 μg of HBsAg with antigen alone or in combination with CpG 24555, 10103 or 7909 (10 μg). Splenocytes from 2 weeks post boost were re-stimulated with the HBsAg antigen (for CD4) or HBs Class I peptide (for CD8) and CD4 (Panel A) and CD8 (Panel B) T cell populations secreting IFN-γ, TNF-α and/or IL-2 were quantified using flow cytometry.

FIG. 9: Innate immunity in Human PBMC. Human PBMC ($5 \times 10^6$/ml) were incubated with varying concentrations of CPG 10103, CPG 24555 or non-CpG control ODN 22881 for 24 or 48 h. Cell supernatants were collected and assayed for cytokine/chemokine secretion using a commercial ELISA kit. FIG. 9A shows IFN-α, MCP-1 and IP-10 secretion. FIG. 9B shows IL-6, IL-10 and IL-2R secretion.

Figure 10A:
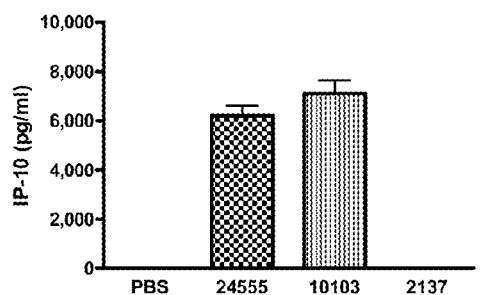
Figure 10B:
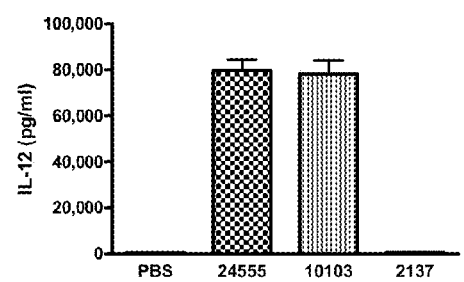
Figure 10C:
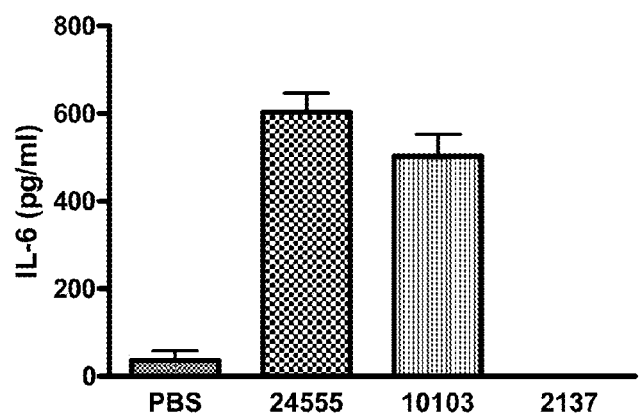

FIG. 10: Innate immunity in vivo in BALB/c mice. BALB/c mice (n=5/group) were injected subcutaneously with PBS (placebo control), CPG 24555, CPG 10103 or non-CpG control ODN 2137 at 100 μg dose level. Animals were bled at 3 hour post injection and plasma assayed for IP-10 (FIG. 10A) and IL-12 (FIG. 10B) or IL-6 (FIG. 10C) using commercial ELISA.

Figure 11A:
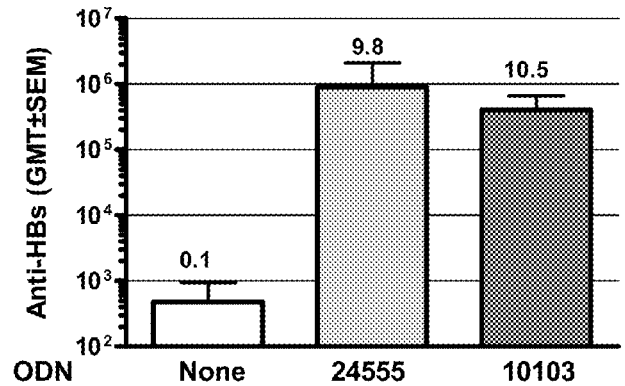
Figure 11B:
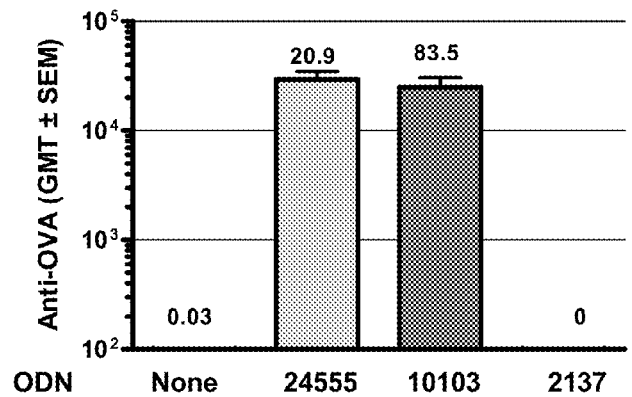
Figure 11C:
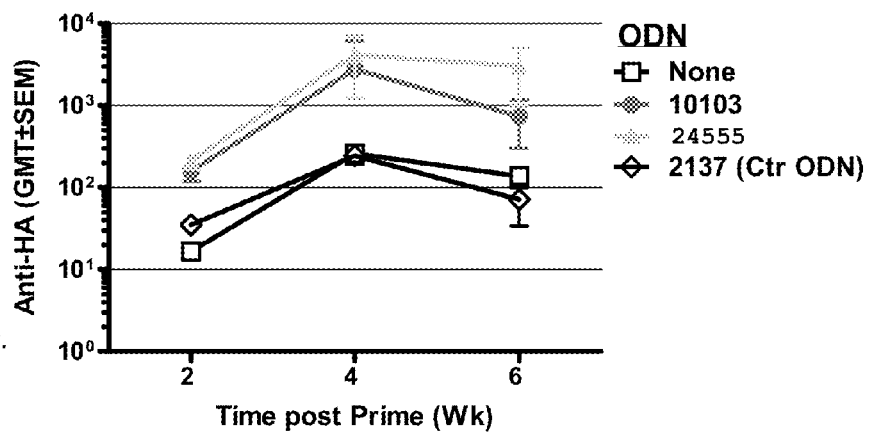

FIG. 11: Humoral immunity in vivo in BALB/c mice. BALB/c mice were immunized intramuscularly with HBsAg (1 μg)±CPG 24555 or 10103 (10 μg), OVA (20 μg)±CPG 24555 or 10103 (10 μg), or with Influenza A HA from Texas 1/77, H3N2 (1 μg)+alum (25 μg Al3+), ±CPG 24555 or 10103 (10 μg). The mice were immunized on 0 and 14 days (HBsAg), on 0, 7 and 21 days (OVA) or on day 0 only (HA). FIG. 11A shows HBsAg specific total IgG titers at 2 weeks post boost measured by endpoint ELISA. FIG. 11B shows OVA specific total IgG titers at 1 week post last boost. FIG. 11C shows kinetics of HA specific total IgG at various times post immunization measured by end point ELISA.

Figure 12A:
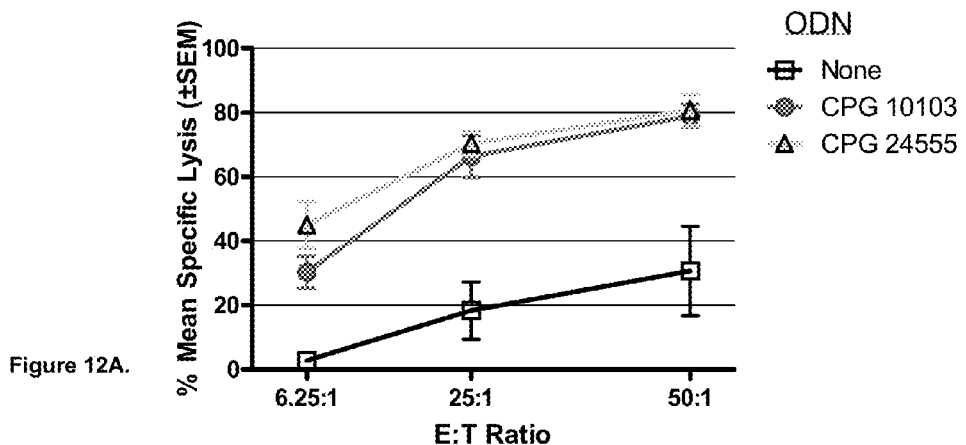
Figure 12B:
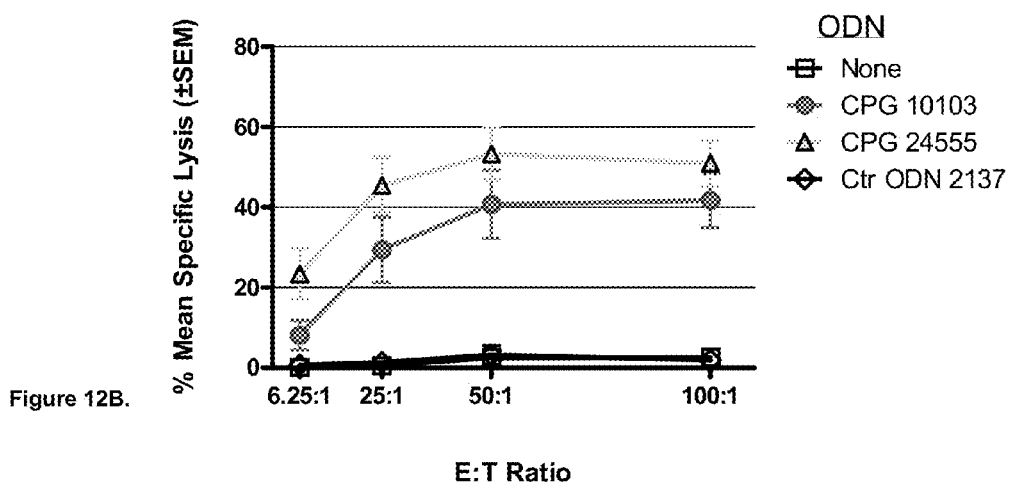

FIG. 12: T cell responses in BALB/c mice. BALB/c mice were injected intramuscularly with HBsAg (1 μg) with or without CPG ODN 2455, CPG 10103 or non-CpG control ODN 2137 at 10 μg. The mice were injected on 0 and 14 days. FIG. 12A shows HBsAg specific CTL measured by $^{51}$Cr release at 2 weeks post boost. C57bl/6 mice were injected intramuscularly with OVA (20 μg) with or without CPG ODN 2455, CPG 10103 or non-CpG control ODN 2137 at 10 μg. The mice were injected on 0, 7 and 21 days. FIG. 12B shows OVA specific CTL measured by $^{51}$Cr release at 1 week post last boost.

Figure 13A:
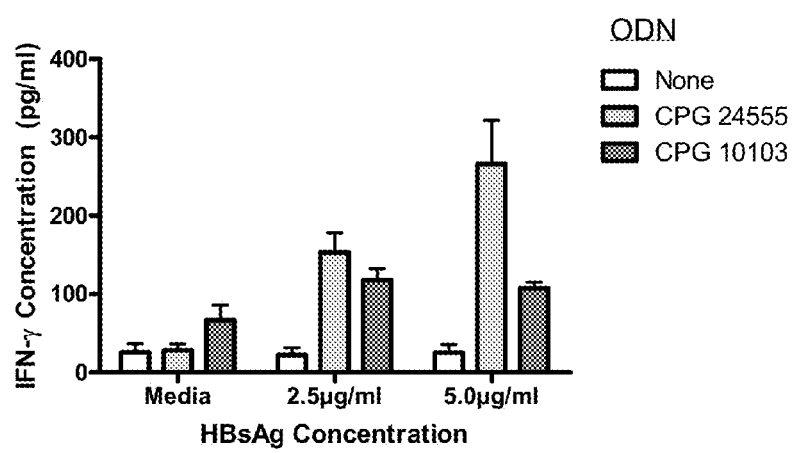
Figure 13B:
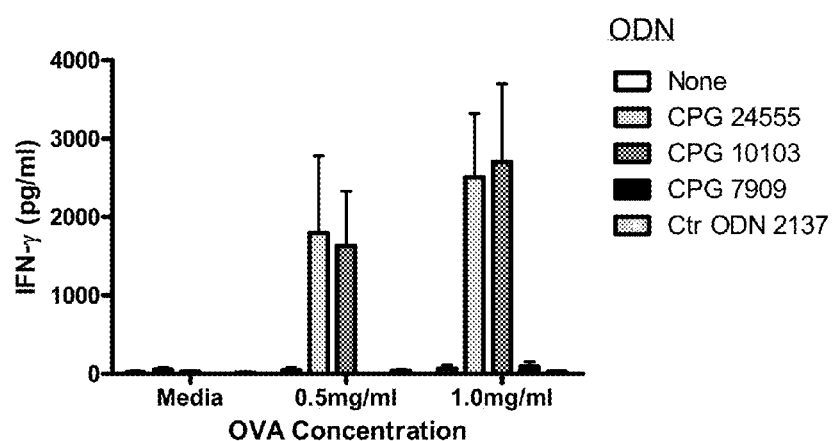

FIG. 13: T cell responses in BALB/c mice. BALB/c mice were injected intramuscularly with HBsAg (1 μg) with or without CPG ODN 2455, CPG 10103 or non-CpG control ODN 2137 at 10 μg. The mice were injected on 0 and 14 days. Splenocytes from 2 week post last boost were incubated with respective antigen for 72 hours and culture supernatants tested for IFN-γ by ELISA (FIG. 13A). C57bl/6 mice were injected intramuscularly with OVA (20 μg) with or without CPG ODN 2455, CPG 10103 or non-CpG control ODN 2137 at 10 μg. The mice were injected on 0, 7 and 21 days. Splenocytes from 1 week post last boost were incubated with respective antigen for 72 hours and culture supernatants tested for IFN-γ by ELISA (FIG. 13B).

Figure 14:
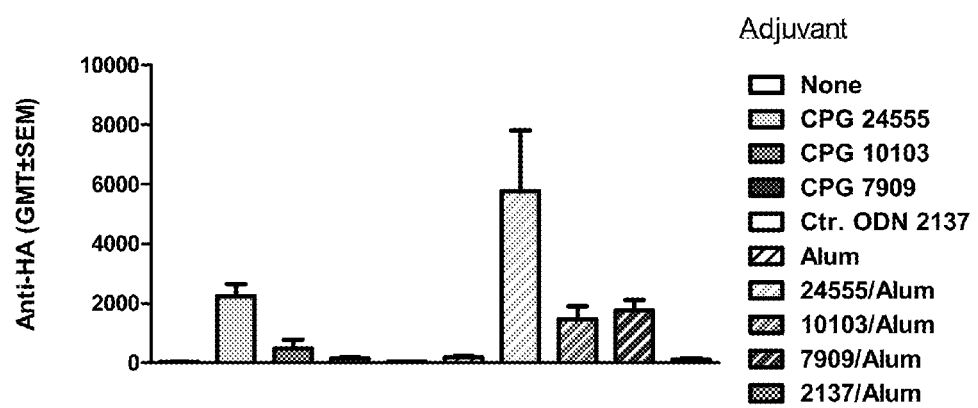

FIG. 14: Anti-HA at 6 Weeks Post Immunization. Female BALB/c mice were immunized with HA (1 μg)±CpG or control ODN (10 μg)±alum (25 μg Al$^{3+}$) in a total volume of 50 μl. The amount of anti-HA was measured at 6 weeks post immunization, FIG. 15: Hemagglutination Inhibition (HIA) Titers at 4 Weeks Post Immunization. The functionality of the antibodies were evaluated using a hemagglutination inhibition assay (HIA). The ability to augment HIA titers alone or in combination with alum was measured.

Figure 16:
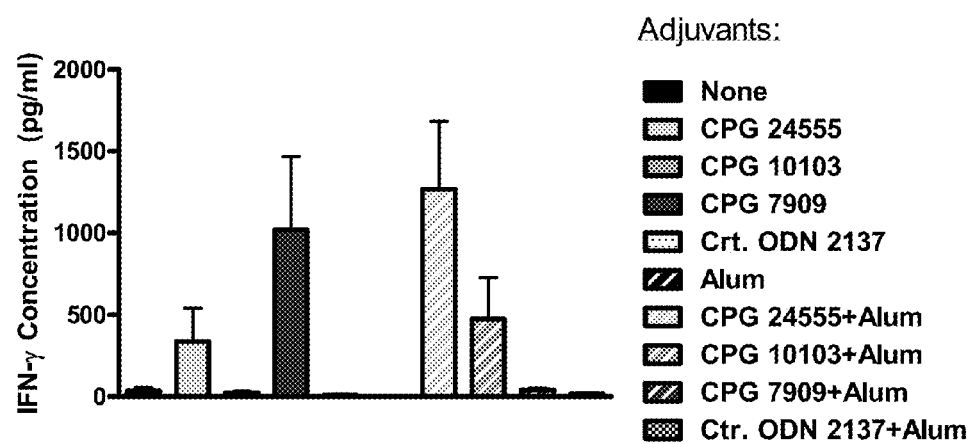

FIG. 16: HA-Specific IFNγ Secretion. Female BALB/c mice were immunized with HA (1 μg)±CpG or control ODN (10 μg)±alum (25 μg Al$^{3+}$) in a total volume of 50 μl. Splenocytes removed at 6 weeks post immunization were used to assay for antigen specific IFNγ secretion.

Figure 17:
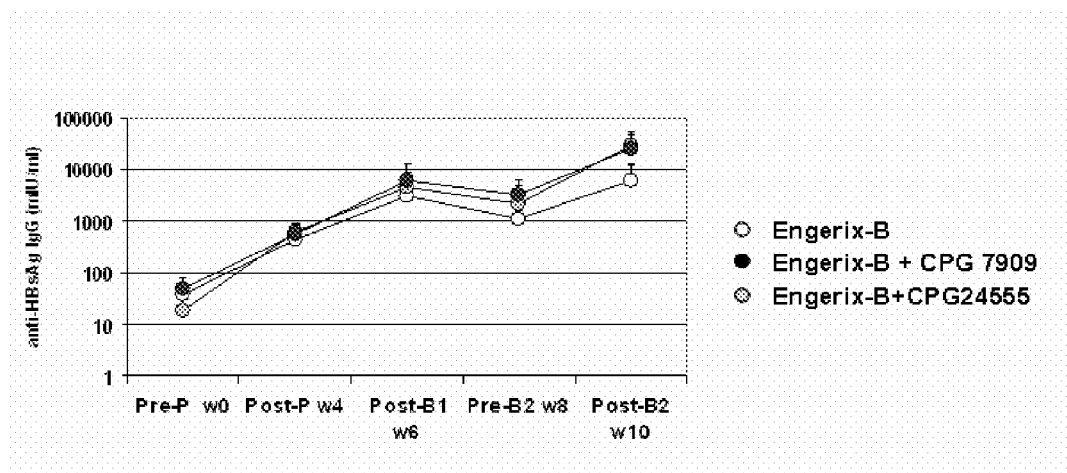

FIG. 17: Humoral Responses in non human primates. Cynomolgus monkeys (3-5 yrs of age; n=5 per group) were immunized with Engerix-B (10 µg HBsAg; 250 µAl$^{3+}$) alone or in combination with 0.5 mg pf CPG 7909 or CPG 24555 by intramuscular injection on weeks 0, 4 and 8. Animals were bled at regular time intervals and HBsAg-specific antibody titer was measured using commercially available kits (MONOLISAT™ Anti-HBS).

Figure 18:
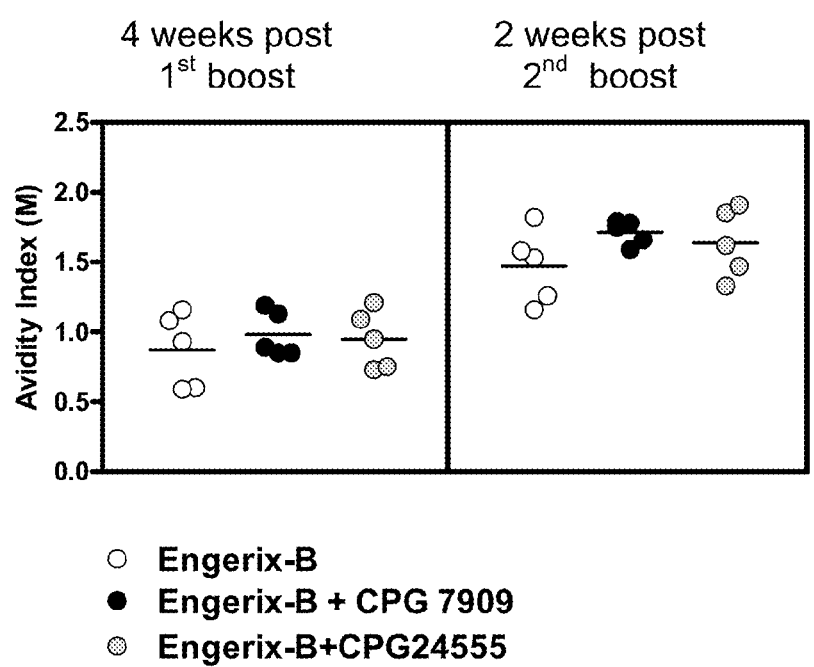

FIG. 18: Humoral Responses in non human primates. Cynomolgus monkeys (3-5 yrs of age; n=5 per group) were immunized with Engerix-B (10 µg HBsAg; 250 µg Al$^3$) alone or in combination with 0.5 mg of CPG 7909 or CPG 24555 by intramuscular injection on weeks 0, 4 and 8, Plasma from 4 weeks post 2$^{nd}$ immunization and 2 weeks post 3$^{rd}$ immunization were assayed for antibody avidity using sodium thiocyanate elusion method.

Figure 19A:
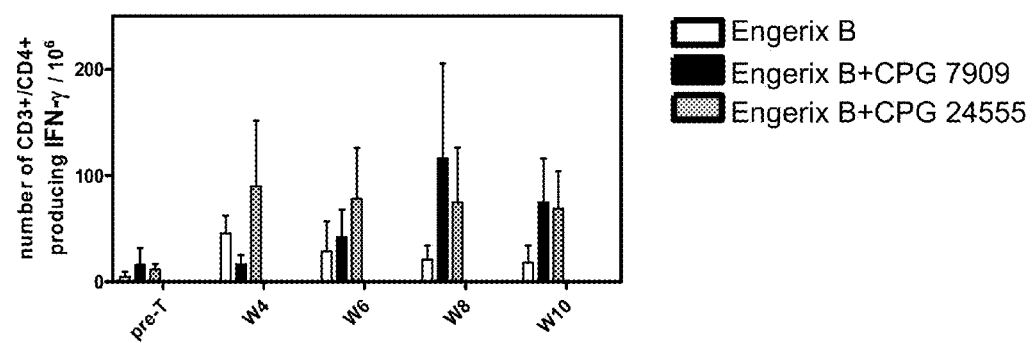
Figure 19B:
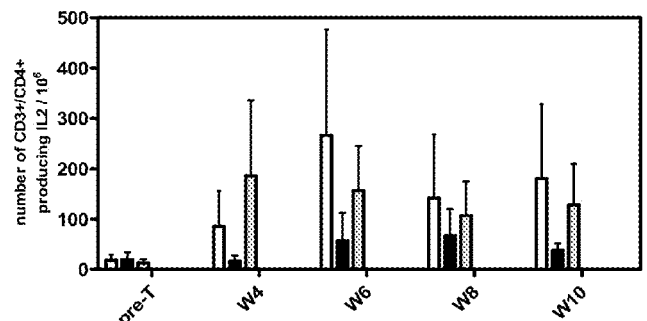
Figure 19C:
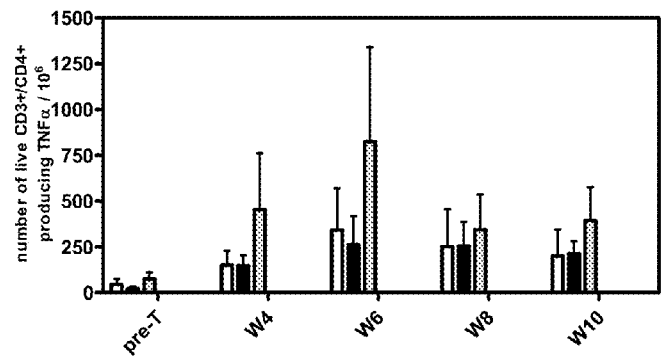

FIG. 19: T Cell Responses in non human primates: Cynomolgus monkeys (3-5 yrs of age; n=5 per group) were immunized with Engerix-B (10 µg HBsAg; 250 µg Al$^3$) alone or in combination with 0.5 mg of CPG 7909 or CPG 24555 by intramuscular injection on weeks 0, 4 and 8, Peripheral blood mononuclear cells (PBMC) at pre vaccination and at several time points post vaccination were tested for HBsAg specific CD4 T cell mediated Intracellular cytokine secretion by flow cytometry. FIG. 19A shows IFN-γ secretion. FIG. 19B shows IL-2 secretion. FIG. 19C shows TNF-α secretion.

Figure 20:
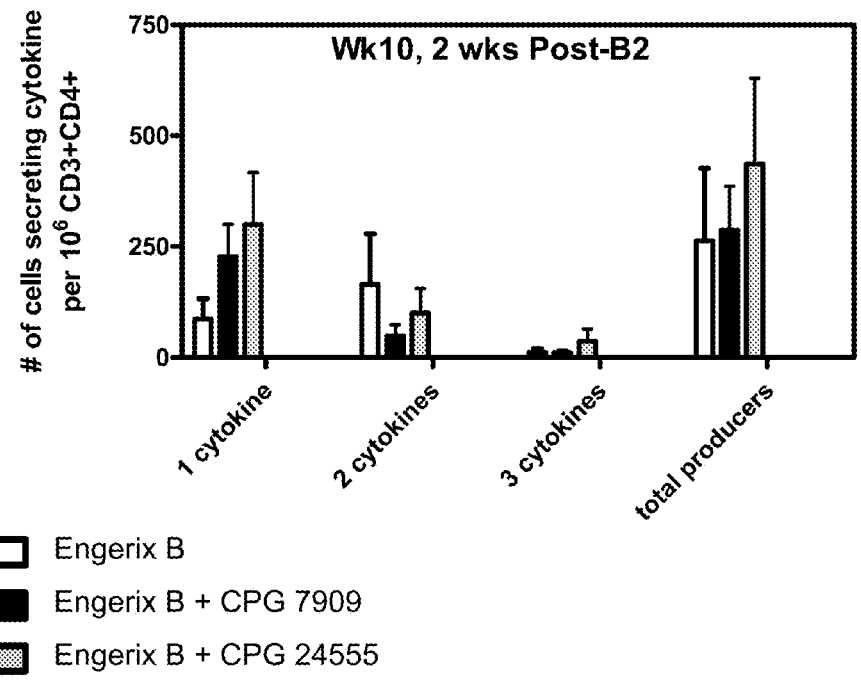
Figure 20:
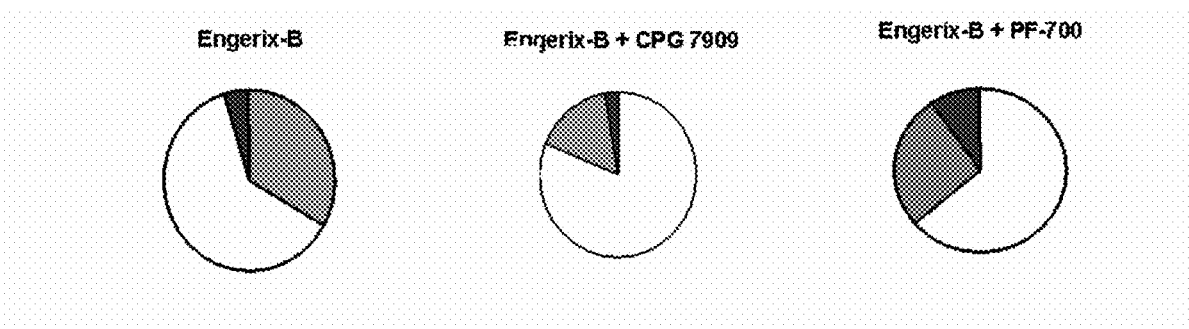

FIG. 20: T Cell Responses: Poly Functional CD4 T Cells; Quantitative Analysis. Cynomolgus monkeys (3-5 yrs of age; n=5 per group) were immunized with Engerix-B (10 µg HBsAg; 250 µg Al$^3$) alone or in combination with 0.5 mg of CPG 7909 or CPG 24555 by intramuscular injection on weeks 0, 4 and 8, Peripheral blood mononuclear cells (PBMC) at 2 weeks post 3$^{rd}$ immunization were tested for HBsAg specific CD4 T cells secreting one, two or three cytokines by flow cytometry. FIG. 20A shows the number of number of HBsAg specific CD4 T cells secreting one, two or three cytokines per one million CD4 T cells analysed. FIG. 20B shows proportion of single, double and triple cytokine producing T cells within total HBsAg specific CD4 T cell population.

FIG. 21: T Cell Responses: poly functional CD4 T cells; Qualitatitve Analysis. The number of cells secreting IL-2, IFN-γ and TNFα, or combinations of these cytokines, was measured. Cynomolgus monkeys (3-5 yrs of age; n=5 per group) were immunized with Engerix-B (10 µg HBsAg; 250 µAl$^3$) alone or in combination with 0.5 mg of CPG 7909 or CPG 24555 by intramuscular injection on weeks 0, 4 and 8, Peripheral blood mononuclear cells (PBMC) at 2 weeks post 3$^{rd}$ immunization were tested for number of HBsAg specific CD4 T cells secreting IL-2, IFN-γ and TNFα, or combinations of these cytokines by flow cytometry.

DESCRIPTION OF SEQUENCES

SEQ ID NO:1—Nucleotide sequence of immunostimulatory oligonucleotide ODN CPG 24555.

SEQ ID NO:2—Nucleotide sequence of immunostimulatory oligonucleotide CPG 10103.

SEQ ID NO:3—Nucleotide sequence of immunostimulatory oligonucleotide CPG 7909.

SEQ ID NO:4—Nucleotide sequence of non-CpG oligonucleotide 22881.

SEQ ID NO:5—Nucleotide sequence of non-CpG oligonucleotide 2137.

DETAILED DESCRIPTION OF THE INVENTION

Aspects of the invention are based, in part, on the surprising discovery that the removal of a CpG motif from an immunostimulatory oligonucleotide did not have a negative impact on the ability of the immunostimulatory oligonucleotide to augment antigen-specific immune responses. It has also been surprisingly found that the removal of said CpG motif allows the generation of an antigen-specific T cells population which is different. In particular it has been found that said antigen-specific T cells population comprises more IFN-gamma secreting T cells and more poly-functional T cells.

In aspects of the invention, the immunostimulatory oligonucleotide has the nucleic acid sequence 5' TCGTCGTTTTTCGGTGCTTTT 3' (ODN CPG 24555; SEQ ID NO:1). The immunostimulatory oligonucleotide nucleic acid sequence of SEQ ID NO:1 differs from a previously reported immunostimulatory oligonucleotide (ODN 10103) 5' TCGTCGTTTTTCGGTCGTTTT 3' (SEQ ID NO:2) by the reversal of the 3' most CG dinucleotide. The similarities in activity between the two immunostimulatory oligonucleotides is surprising because it has been previously reported that immunostimulatory activity of CpG oligonucleotides is dependent on the number of CpG motifs, the sequences flanking the CG dinucleotide, the location of the CpG motif(s) and the spacing between the CpG motifs (Ballas et al., 1996, J. Immunol. 157 (5): 1840-5; Hartmann et al., 2000, J. Immunol., 164 (3): 1617-24; Klinman et al., 2003, Clin. Exp. Immunol., 133 (2): 227-32). The removal of the 3' most CG dinucleotide in immunostimulatory oligonucleotide CPG ODN 24555 (SEQ ID NO:1) did not result in a negative impact on the ability of this immunostimulatory oligonucleotide to augment antigen-specific immune responses as would have been expected from previous disclosures. CPG ODN 24555 demonstrated similar and, in some cases, enhanced immunostimulatory activity when compared with CPG ODN 10103.

In addition, it has been found that CPG ODN 24555 induces a different population of antigen-specific T cells as compared to CPG ODN 10103 (see FIG. 8, table 1 and table 2). In particular, it has been surprisingly found that the antigen-specific T cells population (in particular the antigen-specific CD4+ T cell population) generated using CPG ODN 24555 as adjuvant comprises more IFN-gamma secreting T cells and more poly-functional T cells as compared to the antigen-specific T cells population generated using CPG ODN 10103 or CPG ODN 7909.

For example a higher proportion of antigen-specific CD4+ T cells producing IFN-γ were obtained when compared to antigen-specific CD4+ T cells population obtained with CpG ODN 10103. Also a higher proportion of poly-functional antigen-specific CD4+ T cells producing both IFN-γ and TNF-α, both IFN-γ and IL-2 or both TNF-α and IL-2, or even triple-producers secreting IFN-γ TNF-α and IL-2 was obtained when compared to the antigen-specific CD4+ T cells population obtained with CPG ODN 10103 or CPG ODN 7909. Also a higher proportion of antigen-specific CD8+ T cells producing TNF-α were obtained when compared to antigen-specific CD8+ T cells population obtained with CPG ODN 10103. A higher proportion of antigen-specific CD8+ T cells producing both IFN-γ and IL-2, both TNF-α and IL-2, or even triple-producers secreting IFN-γ, TNF-α and IL-2 was also obtained when compared to the antigen-specific CD8+ T cells population obtained with CPG ODN 10103 or CPG ODN 7909.

The importance of the poly-functionality of T cells in immunogenicity has been highlighted recently. In particular poly-functionality of antigen specific T cells in terms of chemokine production (such as IFN-γ, TNF-α and IL-2) has been correlated in some instances to their protective potential (see e.g. Harari A, et al., Immunol Rev. 2006; 211:236-54, Makedonas G and Betts MR. Springer Semin Immunopathol. 2006; 28(3):209-19, Precopio M L et al., J Exp Med. 2007 204 (6):1405-16, Xu R et al. Vaccine. 2008; 26(37):4819-29) thought to be due to their better effector function compared to T cells that secrete but a single cytokine.

CPG ODN 24555 advantageously allows generating poly-functional antigen-specific T cells populations when used as an adjuvant which can be of importance in a vaccine setting.

The immunostimulatory nucleic acids can be double-stranded or single-stranded. Generally, double-stranded molecules are more stable in vivo, while single-stranded molecules have increased immune activity. In some aspects of the invention it is preferred that the nucleic acid be single stranded and in other aspects it is preferred that the nucleic acid be double-stranded.

The terms "nucleic acid" and "oligonucleotide" are used interchangeably herein to mean multiple nucleotides (i.e., molecules comprising a sugar (e.g., ribose or deoxyribose) linked to a phosphate group and to an exchangeable organic base, which is either a substituted pyrimidine (e.g., cytosine (C), thymidine (T) or uracil (U)) or a substituted purine (e.g., adenine (A) or guanine (G)). As used herein, the terms refer to oligodeoxyribonucleotides, oligoribonucleotides (i.e., a polynucleotide minus the phosphate) and any other organic base containing polymer. Nucleic acid molecules can be obtained from existing nucleic acid sources (e.g., genomic or cDNA), but are preferably synthetic (e.g., produced by nucleic acid synthesis).

In aspects of the invention, the immunostimulatory oligonucleotides can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example in Uhlmann E. et al. (1990), Chem. Rev. 90:543; "Protocols for Oligonucleotides and Analogs" Synthesis and Properties & Synthesis and Analytical Techniques, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. An oligonucleotide according to the invention may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In aspects of the invention, the oligonucleotides may comprise one or more modifications. Such modifications may be selected from: a) the replacement of a phosphodiester internucleoside bridge located at the 3' and/or the 5' end of a nucleoside by a modified internucleoside bridge, b) the replacement of phosphodiester bridge located at the 3' and/or the 5' end of a nucleoside by a dephospho bridge, c) the replacement of a sugar phosphate unit from the sugar phosphate backbone by another unit, d) the replacement of a β-D-ribose unit by a modified sugar unit, and e) the replacement of a natural nucleoside base.

Nucleic acids also include substituted purines and pyrimidines, such as C-5 propyne pyrimidine and 7-deaza-7-substituted purine modified bases (Wagner et al., 1996, Nat. Biotechnol. 14:840-4). Purines and pyrimidines include, but are not limited to, adenine, cytosine, guanine, thymidine, 5-methlycytosine, 2-aminopurine, 2-amino-6-chloropurine, 2,6-diaminoputine, hypoxanthine, and other naturally and non-naturally occurring nucleobases, substituted and unsubstituted aromatic moieties. Other such modifications are well known to those of skill in the art.

A modified base is any base which is chemically distinct from the naturally occurring bases typically found in DNA and RNA, such as T, C, G, A, and U, but which share basic chemical structures with these naturally occurring bases. The modified nucleoside base may be, for example, selected from hypoxanthine, dihydrouracil pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkylnyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkylnylcytosine, 5-chlorocytosine, 5-fluorocytosine, 5-bromocytosine, $N^2$-dimethylguanine, 2,4-dimaino-purine, 8-azapurine, a substituted 7-deazapurine, preferably 7-deaza-7-substituted and/or 7-deaza-8-substituted purine, 5-hydroxymethlycytosine, N4-alkylcytosine (e.g., N4-ethylcytosine), 5-hydroxydeoxycytidine, 5-hydroxymethyldeoxycytidine, N4-alkyldeoxycytidine (e.g., N4-ethyldeoxycytidine), 6-thiodeoxyguanosine, deoxyribonucleosides of nitropyrrole, C5-propynylpyrimisine, diaminopurine (e.g., 2,6-diaminopurine), inosine, 5-methylcytosine, 2-aminopurine, 2-amino-6-chloropurine, hypoxanthine or other modifications of a natural nucleoside base. This list is meant to be exemplary and is not to be interpreted to be limiting.

In some aspects of the invention, the CpG dinculeotide of the immunostimulatory oligonucleotides described herein are preferably unmethylated. An unmethylated CpG motif is an unmethylated cytosine-guanine dinucleotide sequence (i.e., an unmethylated 5' cytosine followed by 3' guanosine and linked by a phosphate bond). In other aspects, the CpG motifs are methylated. A methylated CpG motif is a methylated cytosine-guanine dinucleotide sequence (i.e., a methylated 5' cytosine followed by a 3' guanosine and linked by a phosphate bond).

In some aspects of the invention, an immunostimulatory oligonucleotide can contain a modified cytosine. A modified cytosine is a naturally occurring or non-naturally occurring pyrimidine base analog of cytosine which can replace this base without impairing the immunostimulatory activity of the oligonucleotide. Modified cytosines include but are not limited to 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine). Some of the preferred cytosines include 5-methyl-cytosine, 5-fluoro-cytosine, 5-hydroxy-cytosine, 5-hydroxymethyl-cytosine, and N4-ethyl-cytosine. In another embodiment of the invention, the cytosine base is substituted by a universal base (e.g. 3-nitropyrrole, P-base), an aromatic ring system (e.g. fluorobenzene or difluorobenzene) or a hydrogen atom (dSpacer). In some aspects, an immunostimulatory oligonucleotide can contain uracil and/or its derivatives (e.g., 5-fluoro-uracil, 5-bromo-uracil, 5-bromovinyl-uracil, 4-thio-uracil, 5-hydroxy-uracil, 5-propynyl-uracil).

In some aspects of the invention, an immunostimulatory oligonucleotide can contain a modified guanine. A modified guanine is a naturally occurring or non-naturally occurring purine base analog of guanine which can replace this base without impairing the immunostimulatory activity of the oligonucleotide. Modified guanines include but are not limited to 7-deazaguanine, 7-deaza-7-substituted guanine, hypoxanthine, N2-substituted guanines (e.g., N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g., N6-methyl-adenine, 8-oxo-adenine), 8-substituted guanine (e.g., 8-hydroxyguanine or 8-bromoguanine), and 6-thioguanine. In another embodiment of the invention, the guanine base is substituted by a universal base (e.g., 4-methyl-indole, 5-nitro-indole, or K-base), an aromatic ring system (e.g., benzimidazole or dichloro-benzimidazole, 1-methyl-1H-[1,2,4]triazole-3-carboxylic acid amide) or a hydrogen atom (dSpacer).

In certain aspects, the oligonucleotides may include modified internucleotide linkages. These modified linkages may be partially resistant to degradation (e.g., are stabilized). A "stabilized nucleic acid molecule" shall mean a nucleic acid molecule that is relatively resistant to in vivo degradation (e.g., via an exo- or endo-nuclease). Stabilization can be a function of length or secondary structure. Nucleic acids that are tens to hundreds of kilobases long are relatively resistant to in vivo degradation. For shorter nucleic acids, secondary structure can stabilize and increase their effect. The formation of a stem loop structure can stabilize a nucleic acid molecule. For example, if the 3' end of a nucleic acid has self-complementarity to an upstream region so that it can fold back and form a stem loop structure, then the nucleic acid can become stabilized and exhibit more activity.

Nucleic acid stabilization can also be accomplished via phosphate backbone modifications. Oligonucleotides having phosphorothioate linkages, in some embodiments, may provide maximal activity and protect the oligonucleotide from degradation by intracellular exo- and end-nucleases.

For use in vivo, nucleic acids are preferably relatively resistant to degradation (e.g., via endo- and exo-nucleases). It has been demonstrated that modification of the nucleic acid backbone provides enhanced activity of nucleic acids when administered in vivo. Secondary structures, such as stem loops, can stabilize nucleic acids against degradation. Alternatively, nucleic acid stabilization can be accomplished via phosphate backbone modifications. A preferred stabilized nucleic acid has at least a partial phosphorothioate modified backbone. Phosphorothioates may be synthesized using automated techniques employing either phosphoramidate or H-phosphonate chemistries. Aryl- and alkyl-phosphonates can be made for example, as described in U.S. Pat. No. 4,469,863; and alkylphosphotriesters (in which the charged oxygen moiety is alkylated as described in U.S. Pat. No. 5,023,243 and European Patent No. 092,574) can be prepared by automated solid phase synthesis using commercially available reagents. Methods for making other DNA backbone modifications and substitutions have been described (Uhlmann, E. and Peyman, A. (1990) Chem. Rev. 90:544; Goodchild, J. (1990) Bioconjugate Chem. 1:165). 2'-O-methyl nucleic acids with CpG motifs also cause immune activation, as do ethoxy-modified CpG nucleic acids. In fact, no backbone modifications have been found that completely abolish the CpG effect, although it is greatly reduced by replacing the C with a 5-methyl C. Constructs having phosphorothioate linkages provide maximal activity and protect the nucleic acid from degradation by intracellular exo- and endo-nucleases. Other modified nucleic acids include phosphodiester modified nucleic acids, combinations of phosphodiester and phosphorothioate nucleic acid, methylphosphonate, methylphosphorothioate, phosphorordithioate, p-ethoxy, and combinations thereof. Each of these combinations and their particular effects on immune cells is discussed in more detail with respect to CpG nucleic acids in PCT Published Patent Applications PCT/US95/01570 (WO 96/02555) and PCT/US97/19791 (WO 98/18810) and in U.S. Pat. No. 6,194,388 B1 issued on Feb. 27, 2001 and U.S. Pat. No. 6,239,116 B1 issued on May 29, 2001. It is believed that these modified nucleic acids may show more stimulatory activity due to enhanced nuclease resistance, increased cellular uptake, increased protein binding, and/or altered intracellular localization.

For administration in vivo, nucleic acids may be associated with a molecule that results in a higher affinity binding to a target cell (e.g., B-cell, monocytic cell or natural killer (NK) cell) surfaces and/or increased cellular uptake by target cells to form a "nucleic acid delivery complex". Nucleic acids can be ionically or covalently associated with appropriate molecules using techniques which are well known in the art. A variety of coupling or crosslinking agents can be used such as, protein A, carbodiimide, or N-succinimidyl-3-(2-pyridyldithio)propionate (SPDP). Nucleic acids can alternatively be encapsulated in liposomes or virosomes using well-known techniques.

Other stabilized nucleic acids include, but are not limited to, nonioninc DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain a diol, such as tetraethyleneglycol or hexaethyleneglycol, at either or both termini have also been shown to be substantially resistant to nuclease degradation. In some embodiments, an immunostimulatory oligonucleotide of the invention may include at least one lipophilic substituted nucleotide analog and/or a pyrimidine-purine dinucleotide.

The oligonucleotides may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'3'-linkage may be a phosphodiester, phosphorothioate or any other modified internucleoside bridge. Methods for accomplishing such linkages are known in the art. For instance, such linkages have been described in Seliger, H. et al., Oligonucleotide analogs with terminal 3'-3'- and 5'-5'-internucleotidic linkages as antisense inhibitors of viral gene expression, Nucleosides & Nucleotides (1991), 10 (1-3), 469-77 and Jiang, et al., Pseudo-cyclic oligonucleotides: in vitro and in vivo properties, Bioorganic & Medicinal Chemistry (1999), 7(12), 2727-2735.

Additionally, 3'3'-linked oligonucleotides where the linkage between the 3' terminal nucleosides is not a phosphodiester, phosphorothioate or other modified bridge, can be prepared using an additional spacer, such as tri- or tetra-ethylenglycol phosphate moiety (Durand, M. et al., Triple-helix formation by an oligonucleotide containing one (dA)12 and two (dT)12 sequences bridged by two hexaethylene glycol chains, Biochemistry (1992), 31 (38), 9197-204, U.S. Pat. No. 5,658,738, and U.S. Pat. No. 5,668,265). Alternatively, the non-nucleotidic linker may be derived from ethanediol, propanediol, or from an abasic deoxyribose (dSpacer) unit (Fontanel, Marie Laurence et al., Sterical Recognition by T4 polynucleotide kinase of non-nucleosidic moieties 5'-attached to oligonucleotides; Nucleic Acids Research (1994), 22 (11), 2022-7) using standard phosphoramidite chemistry. The non-nucleotidic linkers can be incorporated once or multiple times, or combined with each other allowing for any desirable distance between the 3'-ends of the two oligonucleotides to be linked.

A phosphodiester internucleoside bridge located at the 3' and/or the 5' end of a nucleoside can be replaced by a modified internucleoside bridge, wherein the modified internucleoside bridge is for example selected from phosphorothioate, phosphorodithioate, $NR^1R^2$-phosphoramidate, boranophosphate, α-hydroxybenzyl phosphonate, phosphate-$(C_1$-$C_{21})$—O—alkyl ester, phosphate-$[(C_6$-$C_{12})$aryl-$(C_1$-$C_{21})$—O-alkyl]ester, $(C_1$-$C_8)$alkylphosphonate and/or $(C_6$-$C_{12})$arylphosphonate bridges, $(C_7$-$C_{12})$-α-hydroxymethyl-aryl (e.g., as disclosed in WO 95/01363), wherein $(C_6$-$C_{12})$aryl, $(C_6$-$C_{20})$aryl and $(C_6$-$C_{14})$aryl are optionally substituted by halogen, alkyl, alkoxy, nitro, cyano, and where $R^1$ and $R^2$ are, independently of each other, hydrogen, $(C_1$-$C_{18})$-alkyl, $(C_6$-$C_{20})$-aryl, $(C_6$-$C_{14})$-aryl, $(C_1$-$C_8)$-alkyl, preferably hydrogen, $(C_1$-$C_8)$-alkyl, preferably $(C_1$-$C_4)$-alkyl and/or methoxyethyl, or $R^1$ and $R^2$ form, together with the nitrogen atom carrying them, a 5 or 6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E. and Peyman A. in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 3'-thioformacetal, methylhydroxylamine, oxime, methylenedimethyl-hydrazo, dimethylenesulfone and/or silyl groups.

The immunostimulatory oligonucleotides of the invention may optionally have chimeric backbones. A chimeric backbone is one that comprises more than one type of linkage. In one embodiment, the chimeric backbone can be represented by the formula: 5' $Y_1N_1ZN_2Y_2$ 3'. $Y_1$ and $Y_2$ are nucleic acid molecules having between 1 and 10 nucleotides. $Y_1$ and $Y_2$ each include at least one modified internucleotide linkage. Since at least 2 nucleotides of the chimeric oligonucleotides include backbone modifications these nucleic acids are an example of one type of stabilized immunostimulatory nucleic acids.

With respect to the chimeric oligonucleotides, $Y_1$ and $Y_2$ are considered independent of one another. This means that each of $Y_1$ and $Y_2$ may or may not have different sequences and different backbone linkages from one another in the same molecule. In some embodiments, $Y_1$ and/or $Y_2$ have between 3 and 8 nucleotides. $N_1$ and $N_2$ are nucleic acid molecules having between 0 and 5 nucleotides as long as $N_1ZN_2$ has at least 6 nucleotides in total. The nucleotides of $N_1ZN_2$ have a phosphodiester backbone and do not include nucleic acids having a modified backbone. Z is an immunostimulatory nucleic acid motif, preferably selected from the immunostimulatory oligonucleotide recited herein.

The center nucleotides $(N_1ZN_2)$ of the formula $Y_1N_1ZN_2Y_2$ have phosphodiester internucleotide linkages and $Y_1$ and $Y_2$ have at least one, but may have more than one or even may have all modified internucleotide linkages. In preferred embodiments, $Y_1$ and/or $Y_2$ have at least two or between two and five modified internucleotide linkages or $Y_1$ has five modified internucleotide linkages and $Y_2$ has two modified internucleotide linkages. The modified internucleotide linkage, in some embodiments, is a phosphorothioate modified linkage, a phosphoroditioate linkage or a p-ethoxy modified linkage.

The nucleic acids also include nucleic acids having backbone sugars which are covalently attached to low molecular weight organic groups other than a hydroxyl group at the 2' position and other than a phosphate group at the 5' position. Thus, modified nucleic acids may include a 2'-O-alkylated ribose group. In addition, modified nucleic acids may include sugars such as arabinose or 2'-fluoroarabinsoe instead of ribose. Thus, the nucleic acids may be heterogeneous in backbone composition thereby containing any possible combination of polymer units linked together such as peptide-nucleic acids (which have an amino acid backbone with nucleic acid bases). In some embodiments, the nucleic acids are homogeneous in backbone composition.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is for example suitable to build up a "morpholino-derivative" oligomer (as described, for example, in Stirchak E. P. et al. (1989) Nucleic Acid Res. 17:6129-41), that is, e.g., the replacement by a morpholino-derivative; or to build up a polyamide nucleic acid ("PNA"; as described, for example, in Nielsen P. E. et al. (1994) Bioconjug. Chem. 5:3-7), that is, for example, the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A βribose unit or a β-D-2' deoxyribose unit can be replaced by a modified sugar unit, wherein the modified sugar unit is for example selected from β-D-ribose, β-D-2'-deoxyribose, L-2'-deoxyribose, 2'-F-2'-deoxyribose, 2'-F-arabinose, 2'-O—$(C_1$-$C_6)$alkyl-ribose, preferably 2'-O—$(C_1$-$C_6)$alkyl-ribose is 2'-O-methylribose, 2'-O—$(C_1$-$C_6)$alkenyl-ribose, 2'-[O—$(C_1$-$C_6)$alkyl-O—$(C_1$-$C_6)$alkyl]-ribose, 2'—$NH_2$-2'-deoxyribose, β-D-xylo-furanose, α-arabinofuranose, 2,4-dideoxy-β-D-erythro-hexo-pyranose, a carbocyclic (described, for example, in Froehler J. (1992) Am. Chem. Soc. 114:8320) and/or open-chain sugar analogs (described, for example, in Vandendriessche et al. (1993) Tetrahedron 49:7223) and/or bicyclosugar analogs (described, for example, in Tarkoy M. et al. (1993) Helv. Chim. Acta. 76:481).

In some embodiments, the sugar is 2'-O-methylribose, particularly for one or both nucleotides linked by a phosphodiester or phosphodiester-like internucleoside linkage.

The oligonucleotides of the invention can be synthesized de novo using any of a number of procedures well known in the art. For example, the b-cyanoethyl phosphoramidite method (Beaucage, S. L., and Caruthers, M. H., (1981) Tet. Let. 22:1859); nucleoside H-phosphonate method (Garegg et al., (1986) Tet. Let. 27:4051-4054; Froehler et al., (1986) Nucl. Acid Res. 14:5399-5407; Garegg et al., (1986) 27:4055-4058; Gaffney et al., (1988) Tet. Let. 29:2619-2622). These chemistries can be performed by a variety of automated nucleic acid synthesizers available in the market. These oligonucleotides are referred to as synthetic oligonucleotides. Alternatively, T-rich and/or TG dinucleotides can be produced on a large scale in plasmids, (see Sambrook T. et al., "Molecular Cloning: A Laboratory Manual", Cold Spring Harbor laboratory Press, New York, 1989) and separated into smaller pieces or administered as whole plasmids. Nucleic acids can be prepared from existing nucleic acid sequences (e.g., genomic or cDNA) using known techniques, such as those employing restriction enzymes, exonucleases or endonucleases.

In an embodiment of the invention, all internucleotide linkages of the immunostimulatory oligonucleotide are phosphorothioate linkages.

Modified backbones such as phosphorothioates may be synthesized using automated techniques employing either phosphoramidate or H-phosphonate chemistries. Aryl- and alkyl-phoshonates can be made, e.g., as described in U.S. Pat. No. 4,469,863, and alkylphosphotriesters (in which the charged oxygen moiety is alkylated as described in U.S. Pat. No. 5,023,243) can be prepared by automated solid phase synthesis using commercially available reagents. Methods for making other DNA backbone modifications and substitutions have been described (e.g. Uhlmann, E. and Peyman, A., Chem. Rev. 90:544, 1990; Goodchild, J., Bioconjugate Chem. 1:165, 1990).

Nucleic acids prepared in this manner are referred to as isolated nucleic acid. An "isolated nucleic acid" generally refers to a nucleic acid which is separated from components with which it is separated from a cell, from a nucleus, from mitochondria or from chromatin and any other components that may be considered as contaminants.

In an embodiment, the immunostimulatory oligonucleotide of the invention consists of 5' T*C*G*T*C*G*T*T*T*T*T*C*G*G*T*G*C*T*T*T*T 3' wherein * indicates phosphorothioate linkage.

In an embodiment, the immunostimulatory oligonucleotide of the invention induces a high proportion of antigen-specific CD4+ T-cells secreting IFN-γ. In an embodiment, the immunostimulatory oligonucleotide of the invention is able to induce at least 40%, preferably at least 45%, even preferably at least 50%, even preferably about 53% of antigen-specific CD4+ T-cells secreting IFN-γ, in the antigen-specific CD4+ T-cell population secreting IFN-γ, TNF-α and/or IL-2. In an embodiment, said proportion of antigen-specific CD4+ T-cells secreting IFN-γ is determined by polychromatic flow cytometry. An example of such determination is disclosed at example 1 of the present document (see paragraph 'Antigen specific multi-cytokine secreting T cell populations').

In an embodiment, the immunostimulatory oligonucleotide of the invention is able to induce at least 10%, preferably at least 15%, even preferably at least 20%, even preferably about 22% of antigen-specific CD4+ T-cells secreting both IFN-γ and TNF-α, in the antigen-specific CD4+ T-cell population secreting IFN-γ, TNF-α and/or IL-2. In an embodiment, said proportion of poly-functional antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations').

In an embodiment, the immunostimulatory oligonucleotide of the invention is able to induce at least 30%, preferably at least 40%, even preferably at least 45%, even preferably about 47% of antigen-specific CD8+ T-cells secreting both IFN-γ and TNF-α, in the antigen-specific CD8+ T-cell population secreting IFN-γ, TNF-α and/or IL-2. In an embodiment, said proportion of poly-functional antigen-specific CD8+ T-cells secreting both IFN-γ and TNF-α is determined by polychromatic flow cytometry. An example of such determination is disclosed at example 1 of the present document (see paragraph 'Antigen specific multi-cytokine secreting T cell populations').

The nucleic acids of the invention can be used as stand alone therapies. A stand alone therapy is a therapy in which a prophylactically or therapeutically beneficial result can be achieved from the administration of a single agent or composition. Accordingly, the nucleic acids disclosed herein can be used alone in the prevention or treatment of infectious disease because the nucleic acids are capable of inducing immune responses that are beneficial to the therapeutic outcome of these diseases. Some of the methods referred to herein relate to the use of the nucleic acids in combination with other therapeutic agents.

The nucleic acids of the invention may be used in a vaccine. When used in a vaccine, the nucleic acid may be administered with an antigen. Preferably the antigen is specific for the disorder sought to be prevented or treated. For example, if the disorder is an infectious disease, the antigen is preferably derived from the infectious organism (e.g., bacterium, virus, parasite, fungus, etc.), if the disorder involves a self antigen (e.g., a tumor, neurodegenerative disorder such as Alzheimer's Disease, an antigen against a human antibody, or an antigen that is expressed from human endogenous retroviral elements), the antigen is preferably derived from the particular disorder associated with the antigen. If the disorder involves an addictive substance, the antigen is preferably derived from the particular additive substance associated with the antigen (e.g., a nicotine hapten).

As used herein, the terms "disorder" and "disease" are used interchangeably.

In an embodiment, the invention pertains to the immunostimulatory oligonucleotide of the invention for use as an adjuvant in a vaccine for the treatment or prevention of a disease, wherein said vaccine comprises at least one antigen and wherein said disease benefits from the generation of polyfunctional antigen specific T cells.

It has been found that CPG ODN 24555 induces a higher proportion of antigen-specific CD4+ T cells producing IFN-γ when compared to antigen-specific CD4+ T cells population obtained with CPG ODN 10103. Also a higher proportion of polyfunctional antigen-specific CD4+ T cells producing both IFN-γ and TNF-α, both IFN-γ and IL-2, both TNF-α and IL-2, or even triple producers of IFN-γ, TNF-α and IL-2 was obtained when compared to the antigen-specific CD4+ T cells population obtained with CPG ODN 10103 or CPG ODN 7909. A higher proportion of polyfunctional antigen-specific CD8+ T cells producing both IFN-γ and IL-2, both TNF-α and IL-2, or even triple producers of IFN-γ TNF-α and IL-2 was also obtained when compared to the antigen-specific CD8+ T cells population obtained with CPG ODN 10103 or CPG ODN 7909.

IFN-γ, TNF-α and IL-2 have been involved in a variety of diseases. For example, TNF-α has been involved in cancer and IFN-γ has been involved in infectious diseases, such as viral infections. Therefore, in an embodiment, the invention pertains to the immunostimulatory oligonucleotide of the invention for use as an adjuvant in a vaccine for the treatment or prevention of cancer. In an embodiment, the invention pertains to the immunostimulatory oligonucleotide of the invention for use as an adjuvant in a vaccine for the treatment or prevention of cancer, wherein said vaccine comprises at least one tumor antigen, preferably any of the tumor antigens disclosed herein.

In an embodiment, the invention pertains to the immunostimulatory oligonucleotide of the invention for use as an adjuvant in a vaccine for the treatment or prevention of an infectious disease. In an embodiment, the invention pertains to the immunostimulatory oligonucleotide of the invention for use as an adjuvant in a vaccine for the treatment or prevention of an infectious disease, wherein said vaccine comprises at least one microbial antigen, preferably any of the microbial antigens disclosed herein.

The immunostimulatory oligonucleotides are useful in some aspects of the invention as a prophylactic vaccine for the prevention of an infection (i.e., an infectious disease), a disorder associated with a self antigen, or a disorder associated with an addictive substance. Preferably, prophylactic vaccination is used in subjects that are not diagnosed with the condition for which the vaccine is sought, and more preferably the subjects are considered at risk of developing one of these conditions. For example, the subject may be one that is at risk of developing an infection with an infectious organism, or susceptible to a disorder associated with a self antigen, or susceptible to a disorder associated with an addictive substance.

A subject at risk, as used herein, is a subject who has any risk of exposure to an infection causing pathogen, a disorder associated with a self antigen or a disorder associated with an addictive substance. A subject at risk also includes subjects that have a predisposition to developing such disorders. Some predispositions can be genetic (and can thereby be identified either by genetic analysis or by family history). Some predispositions are environmental (e.g., prior exposure to infectious agents, self antigens or addictive substances). For a subject at risk of developing an infection, an example of such a subject is a subject living in or expecting to travel to an area where a particular type of infectious agent is or has been found, or it may be a subject who through lifestyle or medical procedures is exposed to an organism either directly or indirectly by contact with bodily fluids that may contain infectious organisms. Subjects at risk of developing infection also include general populations to which a medical agency recommends vaccination for a particular infectious organism.

A subject is a subject treated by veterinarian medicine, a rodent or a non-rodent subject. Non-rodent subjects include, but are not limited to, human or vertebrate animal, such as a dog, a cat, a horse, a cow, a pig, a sheep, a goat, a chicken, a primate (e.g., monkey) and a fish (aquaculture species, e.g., salmon). Rodent subjects include, but are not limited to, rats and mice. In some embodiments, a subject is a human.

The immunostimulatory oligonucleotides can also be given to a subject without an antigen for shorter term protection against infection. In this case, repeated doses will allow for longer term protection.

A subject having an infection is a subject that has been exposed to an infectious pathogen and has acute or chronic detectable levels of the pathogen in the body, or in bodily waste. When used therapeutically, the immunostimulatory oligonucleotides can be used as stand alone or in combination with another therapeutic agent. For example, immunostimulatory oligonucleotides can be used therapeutically with an antigen to mount an antigen specific systemic or mucosal immune response that is capable of reducing the level of, or eradicating, the infectious pathogen.

An infectious disease, as used herein, is a disease arising from the presence of a foreign microorganism in the body. It is particularly important to develop effective vaccine strategies and treatments to protect the body's mucosal surfaces which are the primary site of pathogenic entry.

A disorder associated with a self antigen is any disorder that is caused by an antigen of a subject's own cells or cell products that causes an immune response in said subject. For example, in some embodiments, a self antigen is a tumor antigen, an antigen associated with Alzheimer's Disease, an antigen against an antibody, or an antigen that is expressed from human endogenous retroviral elements. A tumor antigen may be HER2, MAGE, NYESO-1, PSA, CEA or a variant form of EGFR. An antigen associated with Alzheimer's Disease may be tau or β-amyloid. An antigen against an antibody may be an antigen against a human antibody, for example, in some embodiments the antigen is IgE.

In some embodiments, a tumor antigen is MAGE A1, MAGE A2, MAGE A3, MAGE A4, MAGE A6, MAGE A10, MAGE A12, HAGE (CT13), BAGE, BORIS, SSX-2, LAGE-1, CAMEL (LAGE-1 alt reading frame), GAGE 1,2,3, TRAG-3, NY-ESO-1, Melan-A/MART-1, tyrosinase, tyrp1 (gp75), tyrp2, gp100/pmel17, PAP, PSA, CEA, Ep-CAM, PSMA, MUC1, MUC2, HER-2, AFP, EphA2, FGF-5, htert, iCE, Livin (ML-IAP), RAGE, RU2, Survivin, Survivin 2B, WT1, Thomsen-Friedenreich (TF) antigen, 5T4, PSCA, STEAP, TGR, Adipophilin, AIM-2, G250, OGT, TGFaRII, CO-95 (KIAA1416), CO-94 (seb4D), CO-9 (HDAC 5), CO-61 (HIP1R), CO-58 (KNSL6), CO-45, CO-42 (TRIP4), CO-41 (MBD2), Ren-32 (Lamin C), TNKL (BC-203), CO-26 (MNK 1), SDCCAG3, GA733-2, STn, CA125, EGFRvIII, BCR-abl, High Affinity Folate Receptor, Mesothelin, hCG, FAP alpha, Cyclin 1, Topoisomerase, Serpin B5/Maspin, Legumain, CDK4, PRAME, ADAM 17, EDDR1, CDC2, Replication Protein A, CDK2, GM2, Globo H, TF(c), Le$^y$, Tn(c), STn(c), GD2, GD3 or GD3L.

A disorder associated with an addictive substance is any disorder that involves a chemical or biological substance that causes a subject to develop an addiction to an addictive substance. For example, in some embodiments, an addictive substance may be nicotine or cocaine. In some embodiments, a nicotine antigen may be a nicotine hapten conjugated to a carrier. In some embodiments, the carrier to which a nicotine hapten is conjugated is diphtheria toxin.

As used herein, the term "treat", "treated" or "treating" when used with respect to an infectious disease refers to a prophylactic treatment which increases the resistance of a subject (a subject at risk of infection) to infection with a pathogen, or in other words, decreases the likelihood that the subject will become infected with the pathogen as well as a treatment after the subject (a subject who has been infected) has become infected in order to fight the infection, e.g., reduce or eliminate the infection or prevent it from becoming worse.

The term "treat", "treated" or "treating" when used with respect to a disorder associated with a self antigen refers to a prophylactic treatment which increases the resistance of a subject (a subject at risk of a disorder associated with a self antigen) to develop such a disorder or decreases the likelihood that the subject will develop the disorder associated with a self antigen as well as treatment after the subject (a subject at risk of a disorder associated with a self antigen) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to a disorder associated with an addictive substance refers to a prophylactic treatment which increases the resistance of a subject (a subject at risk of a disorder associated with an addictive substance) to develop such a disorder or decreases the likelihood that the subject will develop the disorder associated with an addictive substance as well as treatment after the subject (a subject at risk of a disorder associated with an addictive substance) has developed such a disorder or begun to develop signs or symptoms of developing such a disorder, to reduce the effect of the disorder, e.g., reduce or eliminate the signs or symptoms associated with the disorder or prevent them from becoming worse.

The treatment of a subject or with an immunostimulatory oligonucleotide as described herein, results in the reduction of infection or the complete abolition of the infection, reduction of the signs/symptoms associated with a disorder associated with a self antigen or the complete abolition on the disorder, or reduction of the signs/symptoms associated with a disorder associated with an addictive substance or the complete abolition of the disorder. A subject may be considered as treated if such symptoms related to the infectious disease, disorder associated with a self antigen or disorder associated with an addictive substance are reduced, are managed or are abolished as a result of such treatment. For an infectious disease, such treatment also encompasses a reduction in the amount of infectious agent present in the subject (e.g., such amounts can be measured using standard assays such as ELISA known to those of ordinary skill in the art). For a disorder associated with a self antigen, such treatment also encompasses a reduction in the amount of self antigen present in the subject or a reduction in the immune response induced as a result of the self antigen. For a disorder associated with an addictive substance, such treatment also encompasses a reduction in the signs/symptoms associated with addiction to an addictive substance.

An "antigen" as used herein is a molecule that is capable of provoking an immune response. Antigens include, but are not limited to, cells, cell extracts, proteins, recombinant proteins, purified proteins, polypeptides, peptides, polysaccharides, polysaccharide conjugates, peptide and non-peptide mimics of polysaccharides and other molecules encoded by plasmid DNA, haptens, small molecules, lipids, glycolipids, carbohydrates, whole killed pathogens, viruses and viral extracts, live attenuated virus or viral vector, live attenuated bacteria or a bacterial vector and multicellular organisms such as parasites and allergens. The term antigen broadly includes any type of molecule which is recognized by a host immune system as being foreign. Antigens include, but are not limited to, microbial antigens, self antigens and addictive substances.

In some aspects, an antigen is conjugated to a carrier. In some embodiments, the carrier is diphtheria toxin, or a virus-like particle. In some embodiments, a virus-like particle is comprised of RNA phage Q-β, hepatitis B surface antigen (HBsAg), or hepatitis B core antigen (HBcAg).

A "microbial antigen" as used herein is an antigen of a microorganism and includes, but is not limited to, virus, bacteria, parasites and fungi. In some embodiments, a bacterial antigen is one associated with the bacterium *Staphylococcus aureus*. In other embodiments, a bacterial antigen is one associated with a bacterium that causes dental caries, for example, *Streptococcus mutans, Streptococcus sobrinus, Streptococcus sanguis, Lactobcaillus acidophilis* or *Actinomyces viscosus*. In some embodiments, a bacterial antigen is one associated with a bacterium that causes periodontal disease, for example, *Porphyromonas gingivalis* or *Actinobacillus actinomycetemcomitans*. In some embodiments, a viral antigen is one associated with Respiratory Syncytical Virus (RSV), Herpes Simplex Virus 1 (HSV1), Herpes Simplex Virus 2 (HSV2), or Human Immunodeficiency Virus-1 (HIV-1) or HIV-2. In some embodiments, a parasitic antigen is one associated with a parasite that causes malaria.

Such antigens include the intact microorganism as well as natural isolates and fragments or derivatives thereof and also synthetic compounds which are identical to or similar to natural microorganism antigens and induce an immune response specific for that microorganism. A compound is similar to a natural microorganism antigen if it induces an immune response (humoral and/or cellular) to a natural microorganism antigen. Such antigens are used routinely in the art and are well known to those of ordinary skill in the art.

In some aspects of the invention, the subject is "exposed to" the antigen. As used herein, the term "exposed to" refers to either the active step of contacting the subject with an antigen or the passive exposure of the subject to the antigen in vivo. Methods for the active exposure of a subject to an antigen are well known in the art. In general, an antigen is administered directly to the subject by any means such as intravenous, intramuscular, oral, transdermal, mucosal, intranasal, intratracheal, or subcutaneous administration. The antigen can be administered locally or systemically. Methods for administering the antigen and the immunostimulatory oligonucleotide are described in more detail below. A subject is passively exposed to an antigen if an antigen becomes available for exposure to the immune cells in the body. A subject may be passively exposed to an antigen, for instance, by entry of a foreign pathogen into the body.

The methods in which a subject is passively exposed to an antigen can be particularly dependent on timing of administration of the immunostimulatory oligonucleotide. For instance, in a subject at risk of developing an infectious disease, the subject may be administered the immunostimulatory oligonucleotide on a regular basis when the risk is greatest. Additionally, the immunostimulatory oligonucleotide may be administered to travelers before they travel to foreign lands where they are at risk of exposure to infectious agents. The immunostimulatory oligonucleotide may also be administered to soldiers or civilians at risk of exposure to biowarfare to induce a systemic or mucosal immune response to the antigen when and if the subject is exposed to it.

Examples of viruses that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). In some embodiments, the viruses are Respiratory Syncytical Virus (RSV), Herpes Simplex Virus 1 (HSV1), Herpes Simplex Virus 2 (HSV2), Human Immunodeficiency Virus-1 (HIV1) or HIV2.

Although many of the microbial antigens described herein relate to human disorders, the invention is also useful for treating other non-human vertebrates. Non-human vertebrates are also capable of developing infections which can be prevented or treated with the immunostimulatory nucleic acids disclosed herein. For instance, in addition to the treatment of infectious human diseases, the methods of the invention are useful for treating infections of animals.

Both gram negative and gram positive bacteria serve as antigens in vertebrate animals. Such gram positive bacteria include, but are not limited to, *Pasteurella* species, Staphylococci species, and *Streptococcus* species. Gram negative bacteria include, but are not limited to, *Escherichia coli*, *Pseudomonas* species, and *Salmonella* species. Specific examples of infectious bacteria include but are not limited to, *Helicobacter pyloris, Borelia burgdorferi, Legionella pneumophilia, Mycobacteria* sps. (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira, Rickettsia*, and *Actinomyces israelli*. In some embodiments, a bacterium is one that causes dental caries, for example *Streptococcus mutans, Streptococcus sobrinus, Streptococcus sanguis, Lactobacillus acidophilis*, or *Actinomyces viscosus*. In other embodiments, a bacterium is one that causes periodontal disease, for example *Porphyromonas gingivalis* or *Actinobacillus actinomycetemcomitans*.

Polypeptides of bacterial pathogens include but are not limited to an iron-regulated outer membrane protein (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an ROMP, and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of Ichthyophthirius; and a structural and regulatory protein of *Cytophaga columnari*; and a structural and regulatory protein of *Rickettsia*.

Examples of fungi include *Cryptococcus neoformans, Histoplasma capsulatum, Coccidioides immitis, Blastomyces dermatitidis, Chlamydia trachomatis, Candida albicans*. Other infectious organisms (i.e., protists) include *Plasmodium* spp. such as *Plasmodium falciparum, Plasmodium malariae, Plasmodium ovale, Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*. In some embodiments, a parasite is one associated with malaria. Other medically relevant microorganisms have been described extensively in the literature, e.g., see C. G. A Thomas, Medical Microbiology, Bailliere Tindall, Great Britain 1983.

Many vaccines for the treatment of non-human vertebrates are disclosed in Bennett, K., Compendium of Veterinary Products, 3rd ed. North American Compendiums, Inc., 1995. As discussed above, antigens include infectious microbes such as viruses, parasites, bacteria and fungi and fragments thereof, derived from natural sources or synthetically. Infectious viruses of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are antigens in vertebrate animals include, but are not limited to, members of the family Reoviridae, including the genus Orthoreovirus (multiple serotypes of both mammalian and avian retroviruses), the genus Orbivirus (Bluetongue virus, Eugenangee virus, Kemerovo virus, African horse sickness virus, and Colorado Tick Fever virus), the genus Rotavirus (human rotavirus, Nebraska calf diarrhea virus, simian rotavirus, bovine or ovine rotavirus, avian rotavirus); the family Picornaviridae, including the genus Enterovirus (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus Cardiovirus (Encephalomyocarditis virus (EMC), Mengovirus), the genus Rhinovirus (Human rhinoviruses including at least 113 subtypes; other rhinoviruses), the genus Apthovirus (Foot and Mouth disease (FMDV)); the family Calciviridae, including Vesicular exanthema of swine virus, San Miguel sea lion virus, Feline picornavirus and Norwalk virus; the family Togaviridae, including the genus Alphavirus (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, including the genus Bunyvirus (Bunyamwera and related viruses, California encephalitis group viruses), the genus Phlebovirus (Sandfly fever Sicilian virus, Rift Valley fever virus), the genus Nairovirus (Crimean-Congo hemorrhagic fever virus, Nairobi sheep disease virus), and the genus Uukuvirus (Uukuniemi and related viruses); the family Orthomyxoviridae, including the genus Influenza virus (Influenza virus type A, many human subtypes); Swine influenza virus, and Avian and Equine Influenza viruses; influenza type B (many human subtypes), and influenza type C (possible separate genus); the family paramyxoviridae, including the genus Paramyxovirus (Parainfluenza virus type 1, Sendai virus, Hemadsorption virus, Parainfluenza viruses types 2 to 5, Newcastle Disease Virus, Mumps virus), the genus Morbillivirus (Measles virus, subacute sclerosing panencephalitis virus, distemper virus, Rinderpest virus), the genus Pneumovirus (respiratory syncytial virus (RSV), Bovine respiratory syncytial virus and Pneumonia virus); the family Rhabdoviridae, including the genus Vesiculovirus (VSV), Chandipura virus, Flanders-Hart Park virus), the genus Lyssavirus (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Hepatitis virus, Human enteric corona virus, and Feline infectious peritonitis (Feline coronavirus).

Illustrative DNA viruses that are antigens in vertebrate animals include, but are not limited to, the family Poxyiridae, including the genus Orthopoxvirus (Variola major, Variola minor, Monkey pox Vaccinia, Cowpox, Buffalopox, Rabbitpox, Ectromelia), the genus Leporipoxvirus (Myxoma, Fibroma), the genus Avipoxvirus (Fowlpox, other avian poxvirus), the genus Capripoxvirus (sheeppox, goatpox), the genus Suipoxvirus (Swinepox), the genus Parapoxvirus (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine and monkeys); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus Mastadenovirus (Human subgroups A, B, C, D, E and ungrouped; simian adenoviruses (at least 23 serotypes), infectious canine hepatitis, and adenoviruses of cattle, pigs, sheep, frogs and many other species, the genus Aviadenovirus (Avian adenoviruses); and non-cultivatable adenoviruses; the family Papoviridae, including the genus Papillomavirus (Human papilloma viruses, bovine papilloma viruses, Shope rabbit papilloma virus, and various pathogenic papilloma viruses of other species), the genus Polyomavirus (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus Parvovirus (Feline panleukopenia virus, bovine parvovirus, canine parvovirus, Aleutian mink disease virus, etc). Further, DNA viruses may include viruses which do not fit into the above families such as Kuru and Creutzfeldt-Jacob disease viruses and chronic infectious neuropathic agents (CHINA virus).

In an embodiment, the invention pertains to a method of inducing an antigen-specific immune response comprising administering an antigen and an immunostimulatory oligonucleotide of the invention wherein at least 40%, preferably at least 45%, even preferably at least 50%, even preferably about 53% of the antigen-specific CD4+ T-cells induced secret IFN-γ, in the antigen-specific CD4+ T-cell population secreting IFN-γ, TNF-α and/or IL-2. In an embodiment, said proportion of antigen-specific CD4+ T-cells secreting IFN-γ is determined by polychromatic flow cytometry. An example of such determination is disclosed at example 1 of the present document (see paragraph 'Antigen specific multi-cytokine secreting T cell populations'). In an embodiment, the antigen and immunostimulatory oligonucleotide are administered in an effective amount to induce an antigen-specific immune response in said subject. In an embodiment, the antigen is any of the antigens disclosed herein.

In an embodiment, the invention pertains to a method of inducing an antigen-specific immune response comprising administering an antigen and an immunostimulatory oligonucleotide of the invention wherein at least 10%, preferably at least 15%, even preferably at least 20%, even preferably about 22% of the antigen-specific CD4+ T-cells induced are double cytokine producers, preferentially secreting both IFN-γ and TNF-α, in the antigen-specific CD4+ T-cell population secreting IFN-γ, TNF-α and/or IL-2. In an embodiment, said proportion of antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen and immunostimulatory oligonucleotide are administered in an effective amount to induce an antigen-specific immune response in said subject. In an embodiment, the antigen is any of the antigens disclosed herein.

In an embodiment, the invention pertains to a method of inducing an antigen-specific immune response comprising administering an antigen and an immunostimulatory oligonucleotide of the invention wherein at least 30%, preferably at least 40%, even preferably at least 45%, even preferably about 47% of the antigen-specific CD8+ T-cells induced are double cytokine producers, preferentially secreting both IFN-γ and TNF-α, in the antigen-specific CD8+ T-cell population secreting IFN-γ, TNF-α and/or IL-2. In an embodiment, said proportion of antigen-specific CD8+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen and immunostimulatory oligonucleotide are administered in an effective amount to induce an antigen-specific immune response in said subject. In an embodiment, the antigen is any of the antigens disclosed herein.

In an embodiment, the invention pertains to the immunostimulatory oligonucleotide of the invention for use in inducing an immune response against an antigen, wherein at least 40%, preferably at least 45%, even preferably at least 50%, even preferably about 53% of the antigen-specific CD4+ T-cells induced secret IFN-γ, in the antigen-specific CD4+ T-cell population secreting IFN-γ, TNF-α and/or IL-2. In an embodiment, said proportion of antigen-specific CD4+ T-cells secreting IFN-γ is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to the immunostimulatory oligonucleotide of the invention for use in inducing an immune response against an antigen, wherein at least 10%, preferably at least 15%, even preferably at least 20%, even preferably about 22% of the antigen-specific CD4+ T-cells induced are double cytokine producers, preferentially secreting both IFN-γ and TNF-α, in the antigen-specific CD4+ T-cell population secreting IFN-γ, TNF-α and/or IL-2. In an embodiment, said proportion of antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to the immunostimulatory oligonucleotide of the invention for use in inducing an immune response against an antigen, wherein at least 30%, preferably at least 40%, even preferably at least 45%, even preferably about 47% of the antigen-specific CD8+ T-cells induced are double cytokine producers, preferentially secreting both IFN-γ and TNF-α, in the antigen-specific CD8+ T-cell population secreting IFN-γ, TNF-α and/or IL-2. In an embodiment, said proportion of antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to the immunostimulatory oligonucleotide of the invention for use as an adjuvant in a vaccine wherein said vaccine induces an immune response against an antigen and wherein at least 40%, preferably at least 45%, even preferably at least 50%, even preferably about 53% of the antigen-specific CD4+ T-cells induced secret IFN-γ, in the antigen-specific CD4+ T-cell population secreting IFN-γ, TNF-α and/or IL-2. In an embodiment, said proportion of antigen-specific CD4+ T-cells secreting IFN-γ is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to the immunostimulatory oligonucleotide of the invention for use as an adjuvant in a vaccine wherein said vaccine induces an immune response against an antigen and wherein at least 10%, preferably at least 15%, even preferably at least 20%, even preferably about 22% of the antigen-specific CD4+ T-cells induced are double cytokine producers, preferentially secreting both IFN-γ and TNF-α, in the antigen-specific CD4+ T-cell population secreting IFN-γ, TNF-α and/or IL-2. In an embodiment, said proportion of double-producing antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to the immunostimulatory oligonucleotide of the invention for use as an adjuvant in a vaccine wherein said vaccine induces an immune response against an antigen and wherein at least 30%, preferably at least 40%, even preferably at least 45%, even preferably about 47% of the antigen-specific CD8+ T-cells induced are double cytokine producers, preferentially secreting both IFN-γ and TNF-α, in the antigen-specific CD8+ T-cell population secreting IFN-γ, TNF-α and/or IL-2. In an embodiment, said proportion of double-producing antigen-specific CD8+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to a vaccine comprising an antigen and an immunostimulatory oligonucleotide of the invention for use in inducing an immune response to said antigen wherein at least 40%, preferably at least 45%, even preferably at least 50%, even preferably about 53% of the antigen-specific CD4+ T-cells induced secret IFN-γ, in the antigen-specific CD4+ T-cell population secreting IFN-γ, TNF-α and/or IL-2. In an embodiment, said proportion of antigen-specific CD4+ T-cells secreting IFN-γ is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to a vaccine comprising an antigen and an immunostimulatory oligonucleotide of the invention for use in inducing an immune response to said antigen wherein at least 10%, preferably at least 15%, even preferably at least 20%, even preferably about 22% of the antigen-specific CD4+ T-cells induced are double cytokine producers, preferentially secreting both IFN-γ and TNF-α, in the antigen-specific CD4+ T-cell population secreting IFN-γ, TNF-α and/or IL-2. In an embodiment, said proportion of antigen-specific CD4+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

In an embodiment, the invention pertains to a vaccine comprising an antigen and an immunostimulatory oligonucleotide of the invention for use in inducing an immune response to said antigen wherein at least 30%, preferably at least 40%, even preferably at least 45%, even preferably about 47% of the antigen-specific CD8+ T-cells induced are double cytokine producers, preferentially secreting both IFN-γ and TNF-α, in the antigen-specific CD8+ T-cell population secreting IFN-γ, TNF-α and/or IL-2. In an embodiment, said proportion of antigen-specific CD8+ T-cells secreting both IFN-γ and TNF-α is determined by polychromatic flow cytometry. An example of such determination is disclosed at example 1 of the present document (see paragraph 'Antigen specific multi-cytokine secreting T cell populations'). In an embodiment, the antigen is any of the antigens disclosed herein.

The language "effective amount" of a nucleic acid molecule refers to the amount necessary or sufficient to realize a desired biologic effect. For example, an effective amount of a nucleic acid containing at least one unmethylated CpG for treating a disorder could be that amount necessary to eliminate a microbial infection or a tumor. An effective amount for use as a vaccine adjuvant could be that amount useful for boosting a subjects immune response to a vaccine. An "effective amount" for treating an infectious disease, a disorder associated with a self antigen or a disorder associated with an addictive substance can be that amount useful for inducing an antigen-specific immune response. The effective amount for any particular application can vary depending on such factors as the disease or condition being treated, the particular CpG immunostimulatory oligonucleotide being administered, the size of the subject, or the severity of the disease or condition. One of ordinary skill in the art can empirically determine the effective amount of a particular oligonucleotide without necessitating undue experimentation.

In aspects of the invention, a vaccine may further include an adjuvant. In some embodiments, an adjuvant is an agonist for a Toll-like receptor (TLR) that is not TLR9. An agonist for a TLR in some embodiments is an agonist for TLR3 (for example, stabilized polyI:C), TLR4 (for example, a derivative of lipopolysaccharide (LPS) for example, MPL or GLA), TLR5 (for example, flagellin), TLR7 (for example, a small molecule of the imidazoquinoline family) or TLR8 (for example, a small molecule of the imidazoquinoline family). In some embodiments, the adjuvant is aluminum salt, for example, aluminum hydroxide, an immune stimulatory complex (ISCOM), an oil-in-water or water-in-oil emulsion, a liposome, or a delivery system, for example, a nanoparticle or microparticle.

The term effective amount of a CpG immunostimulatory oligonucleotide refers to the amount necessary or sufficient to realize a desired biologic effect. For example, an effective amount of a CpG immunostimulatory oligonucleotide administered with an antigen for inducing an antigen-specific immune response is that amount necessary to induce an immune response in response to an antigen upon exposure to the antigen. Combined with the teachings provided herein, by choosing among the various active immunostimulatory oligonucleotides and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular CpG immunostimulatory oligonucleotide being administered, the size of the subject, or the severity of the disease or condition. One of ordinary skill in the art can empirically determine the effective amount of a particular CpG immunostimulatory oligonucleotide and/or antigen and/or other therapeutic agent without necessitating undue experimentation in light of this disclosure.

Subject doses of the compounds described herein for local delivery typically range from about 0.1 µg to 50 mg per administration which, depending on the application, could be given daily, weekly, or monthly and any other amount of time therebetween. More typically local doses range from about 10 µg to 10 mg per administration, and optionally from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Subject doses of the compounds described herein for parenteral delivery for the purpose of inducing an antigen-specific immune response, wherein the compounds are delivered with an antigen but not another therapeutic agent are typically 5 to 10,000 times higher than the effective local dose for vaccine adjuvant or immune stimulant applications, and more typically 10 to 1,000 times higher, and most typically 20 to 100 times higher.

Doses of the compounds described herein for parenteral delivery, e.g., for inducing an innate immune response, for increasing ADCC, for inducing an antigen specific immune response when the CpG immunostimulatory oligonucleotides are administered in combination with other therapeutic agents or in specialized delivery vehicles typically range from about 0.1 µg to 10 mg per administration which, depending on the application, could be given daily, weekly, or monthly and any other amount of time therebetween. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

For any compound described herein the therapeutically effective amount can be initially determined from animal models. A therapeutically effective dose can also be determined from human data for CpG oligonucleotides which have been tested in humans (e.g., human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the CpG immunostimulatory oligonucleotide can be administered to a subject by any mode that delivers the oligonucleotide to the desired surface. Administering the pharmaceutical composition of the present invention may be accomplished by any means known to the skilled artisan. Preferred routes of administration include but are not limited to parenteral (for example, intramuscular, subcutaneous, intradermal, intravenous, intravesical or intraperitoneal), topical (for example, skin (transdermal), mucosal), oral, intranasal, intravaginal, intrarectal, trans-buccal, intraocular or sublingual.

The immunostimulatory oligonucleotides either alone or in conjunction with other therapeutic agents, may be administered via any route described herein. In some preferred embodiments, the administration is local. Local administration may include topical application to mucosal surfaces, e.g., the skin, such as those of the mouth and genitals.

The immunostimulatory oligonucleotides, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the immunostimulatory oligonucleotides in water-soluble form. Additionally, suspensions of the immunostimulatory oligonucleotides may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the immunostimulatory oligonucleotides to allow for the preparation of highly concentrated solutions.

The immunostimulatory oligonucleotides, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

One may dilute or increase the volume of the therapeutic with an inert material. These diluents could include carbohydrates, especially mannitol, a-lactose, anhydrous lactose, cellulose, sucrose, modified dextrans and/or starch. Certain inorganic salts may be also be used as fillers including calcium triphosphate, magnesium carbonate and/or sodium chloride. Some commercially available diluents are Fast-Flo, Emdex, STA-Rx 1500, Emcompress and Avicell.

To aid dissolution of the therapeutic into the aqueous environment a surfactant might be added as a wetting agent. Surfactants may include anionic detergents such as sodium lauryl sulfate, dioctyl sodium sulfosuccinate and/or dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and/or 60, glycerol monostearate, polysorbate 40, 60, 65 and/or 80, sucrose fatty acid ester, methyl cellulose and carboxymethyl cellulose. These surfactants could be present in the formulation of the immunostimulatory oligonucleotides either alone or as a mixture in different ratios.

Pharmaceutical formulations for parenteral administration include aqueous solutions of the immunostimulatory oligonucleotides in water-soluble form. Additionally, suspensions of the immunostimulatory oligonucleotides may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the immunostimulatory oligonucleotides to allow for the preparation of highly concentrated solutions.

Alternatively, the immunostimulatory oligonucleotides may be in powder form for constitution with a suitable vehicle, e.g., sterile pyrogen-free water, before use.

For oral administration, the compounds (i.e., CpG immunostimulatory oligonucleotides, antigens and other therapeutic agents) can be formulated readily by combining the immunostimulatory oligonucleotides with pharmaceutically acceptable carriers well known in the art. Such carriers enable the immunostimulatory oligonucleotides of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also contemplated are oral dosage forms of the above agents or formulations. The agents or formulations may be chemically modified so that oral delivery of the derivative is efficacious. Generally, the chemical modification contemplated is the attachment of at least one moiety to the agent or formulation itself, where said moiety permits (a) inhibition of proteolysis; and (b) uptake into the blood stream from the stomach or intestine. Also desired is the increase in overall stability of the agent or formulation and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

Intranasal delivery of a pharmaceutical composition of the present invention is also contemplated. Intranasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For intranasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize an aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when the bottle is squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

For trans-buccal administration, the compositions may take the form of tablets or lozenges formulated in conventional manner.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990.

The CpG immunostimulatory oligonucleotides and optionally other therapeutics and/or antigens may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a CpG immunostimulatory oligonucleotide and optionally antigens and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference in their entireties.

EXAMPLES

Example 1

Immunostimulatory oligonucleotide CPG 24555 was compared with oligonucleotides CPG 10103 and CPG 7909 for their ability to augment antigen-specific immune responses in mice when immunized intramuscularly (IM) using hepatitis B surface antigen (HBsAg) or ovalbumin (OVA) as model antigens.

Methods and Materials

All ODN were prepared from lyophilized oligodeoxynucleotide (ODN). Briefly, ODN were dissolved in endotoxin free Tris-EDTA buffer at pH 8.0 (OmniPur®; EM Science, Gibbstown, N.J.) and diluted in sterile endotoxin-free Phosphate Buffered Saline (PBS) at pH 7.2 (Sigma Chemical Company, St. Louis, Mo.) under aseptic conditions to prevent both microbial and endotoxin contamination. Stock solutions were stored at 4° C. until use.

Female wild type BALB/c and C57Bl/6 mice were purchased from Charles River Canada (Quebec, Canada). TLR9 deficient mice in C57 background were bred at Taconic Farms and transferred to Coley Animal Care Facility for studies. Mice were housed in micro-isolator cages in the Animal Care Facility at Coley Pharmaceutical Group Canada. All studies were conducted in accordance with the Animal Care Committee of Coley Canada under the guidance of Association for assessment and accreditation of laboratory animal care (AAALAC International) and the Canadian Council on Animal Care. Animals were approximately 18-20 g of weight at start of study.

Immunization of Mice

Hepatitis B Surface Antigen (HBsAg)

BALB/c mice (n=10/group) were immunized intramuscularly (IM) in the left tibialis anterior muscle with 1 μg HBsAg; subtype ad (Cliniqa, 4076), alone or in combination with 10 μg CPG 24555, CPG 10103 or CPG 7909 in a total volume of 50 μl. At 2 weeks post prime, animals were bled via the sub-mandibular vein using heparin as an anti-coagulant and boosted using the same vaccine formulation used for the primary immunization. At 2 weeks post-boost, animals were bled by cardiac puncture using heparin as an anti-coagulant, euthanized by cervical dislocation and spleens removed aseptically for use in immune assay for detection of antigen-specific CTL activity, IFN-γ secretion (culture supernatants) and multi-cytokine (IFN-γ, TNF-α and IL-2) secreting CD4 vs CD8 T cells. Plasma from each bleed time point was used for detection of antigen specific total IgG and IgG isotypes IgG1 and IgG2a.

Chicken Ovalbumin (OVA)

C57Bl/6 wild type and TLR9 deficient (C57Bl/6 TLR9−/−) mice (n=10/group) were immunized intramuscularly (IM) in the left tibialis anterior muscle with 20 μg OVA grade VII (Sigma, A7641) alone or in combination with 10 μg CPG 24555, CPG 10103, CPG 7909 or non-CpG control ODN 2137 in a total volume of 50 μl. Animals were boosted using the same vaccine formulation as used for the primary immunization at 14 and 21 days post primary immunization. At 7 days post-last boost, animals were bled through cardiac puncture using heparin as an anti-coagulant, euthanized by cervical dislocation and spleens removed aseptically for use in immune assay for detection of antigen-specific CTL activity, IFN-γ secretion (culture supernatants), tetramer positive CD8 T cells and multi-cytokine (IFN-γ, TNF-α and IL-2) secreting CD4 vs. CD8 T cells. Plasma was used for detection of antigen specific total IgG and IgG isotypes IgG1 and IgG2c.

Immune Assays

Determination of Antigen Specific Antibody Titers

Antibodies (total IgG, IgG1 and IgG2a/c) specific to HBsAg (anti-HBs) or ovalbumin (anti-OVA) were detected and quantified by endpoint dilution ELISA assay, which was performed in triplicate on samples from individual animals. End-point titers were defined as the highest plasma dilution that resulted in an absorbance value (OD 450 nm) two times greater than that of non-immune plasma with a cut-off value of 0.05. These were reported as group geometric mean titers (GMT±SEM.

Evaluation of CTL Responses

Spleens removed at 1 week (for OVA) or 2 week (for HBsAg) post last immunization were used for assay of antigen specific cytotoxic T lymphocyte (CTL) responses. Spleens were homogenized into single cell suspension in RPMI 1640 (Hyclone, Logan, Utah) tissue culture medium supplemented with 10% fetal bovine serum (Hyclone, Logan, Utah), penicillin-streptomycin solution (final concentration of 1000 U/ml and 1 mg/ml respectively; Invitrogen, Burlington, ON), L-glutamine (final concentration of 2 mM; Invitrogen, Burlington, ON) and $5\times10^{-6}$ M β-mercaptoethanol (Invitrogen, Burlington, ON). HBsAg-specific lymphocytes in splenocyte suspensions ($3\times10^6$ cells/ml) were re-stimulated for 5 days by incubating with an irradiated murine cell line (P815/S) expressing HBsAg and OVA-specific lymphocytes in splenocyte suspensions ($3\times10^6$ cells/ml) were re-stimulated for 5 days by incubating with an irradiated murine cell line (EG.7) expressing OVA. Following re-stimulation, the potential of the lymphocytes to kill cells expressing HBsAg or OVA was determined by using $^{51}$Cr release assay. The results are presented as % specific lysis at different effector to target (E:T) ratios.

Evaluation of Antigen Specific IFN-γ Secretion by Splenocytes

Splenocytes from 1 week (for OVA) or 2 week (for HBsAg) post last immunization were used measuring IFN-γ secretion following antigen re-stimulation. Briefly, spleen cell suspensions were prepared as done for CTL assay and adjusted to a final concentration of $5\times10^6$ cells per ml in RPMI 1640 (Hyclone, Logan, Utah) tissue culture medium supplemented with 2% normal mouse serum (Cedarlane Laboratories, Ontario, Canada), penicillin-streptomycin solution (final concentration of 1000 U/ml and 1 mg/ml respectively; Invitrogen, Burlington, ON), L-glutamine (final concentration of 2 mM; Invitrogen, Burlington, ON) and $5\times10^{-5}$ M β-mercaptoethanol (Invitrogen, Burlington, ON) [Complete RPMI 1640]. Splenocyte suspension was plated onto 96-well U-bottom tissue culture plates (100 µl/well) along with 100 µl of each stimulant (as described on appropriate figure legends) diluted to appropriate concentrations in Complete RPMI 1640. Concanavalin A (10 µg/ml, Sigma) was used as a positive control and cells cultured with media alone were used as negative controls. Each splenocyte sample was plated in triplicate and the cells were incubated in a humidified 5% $CO_2$ incubator at 37° C. for 72 hr. Culture supernatants were harvested at the end of the incubation period and stored at −80° C. until assayed. Commercially available assay kits (mouse IFN-γ OptEIA; BD Pharmingen, Mississauga, ON) were used according to manufacturer's instructions to assay IFN-γ levels in culture supernatants.

Quantification of OVA tetramer positive CD8 population

Splenocyte suspensions obtained as described above were also used for quantification of OVA tetramer positive CD8 populations by FACS. Splenocytes ($2\times10^6$) from individual spleens were transferred to 12×75 mm test tubes containing 500 µl of staining buffer: DPBS containing 1% fetal bovine serum (Hyclone, Logan, Utah) and 0.1% Sodium Azide (Sigma). Cells were centrifuged at 1200 rpm for 5 minutes and supernatant removed. Fc receptors were blocked by incubating cells at 4° C. for 10 minutes with anti-mouse CD16/CD32 (Fc block) (BD Pharmingen). Cells were washed with staining buffer and stained for 20 minutes at 4° C. using class-1OVA-specific (SIINFEKL) tetramer (Beckman Coulter). Cells were then washed again with staining buffer and stained for 20 minutes at 4° C. with anti-mouse CD8a-FITC (BD Pharmingen). Cells were washed with staining buffer, resuspended in 500 µl of staining buffer and analyzed using a FC500 flow cytometer (Beckman coulter). OVA-specific CD8 T cells were identified as cells that were both positive for CD8a as well as tetramer. Data is expressed as % CD8 and tetramer positive cells.

Quantification of Antigen Specific Multi-Cytokine Secreting T Cell Populations

Pooled splenocyte suspensions for each group were re-stimulated in 24-well tissue culture plates in RPMI 1640 (Hyclone, Logan, Utah) tissue culture medium supplemented with 2% normal mouse serum (Cedarlane Laboratories, Ontario, Canada), penicillin-streptomycin solution (final concentration of 1000 U/ml and 1 mg/ml respectively; Invitrogen, Burlington, ON), L-glutamine (final concentration of 2 mM; Invitrogen, Burlington, ON) and $5\times10^{-5}$ M β-mercaptoethanol (Invitrogen, Burlington, ON).

For CD4 re-stimulation: $5\times10^6$ cells were stimulated overnight in a final volume of 1 ml containing 5 µg/ml of HBsAg.

For CD8 re-stimulation; $5\times10^6$ cells were stimulated for 5 hours in a final volume of 1 ml containing 5 µg/ml of HBs peptide (IPQSLDSWWTSL).

Media without stimulants was used as negative control where as 10 ng/ml of PMA (Sigma) and 1 µg/ml ionomycin (Sigma) [added during the last 4 hours of incubation] were used as positive controls. Additionally, during the last 4 hours of re-stimulation, Brefelden A (BD Pharmingen) and monensin (BD Pharmingen) were added to halt protein transport.

Following re-stimulation, cells were washed with staining buffer and Fc receptors were blocked by incubating cells at 4° C. for 10 minutes with anti-mouse CD16/CD32 (Fc block) (BD Pharmingen). Cells were then centrifuged and re-suspended in staining buffer containing 5 µg/ml of either anti-mouse CD4-ECD (Invitrogen) or anti-mouse CD8-ECD (Invitrogen) and incubated for 30 minutes at 4° C. Cells were washed with staining buffer and re-suspended in BD Fix/Perm Solution (BD Pharmingen) for 20 minutes at 4° C. Cells were washed again with BD Perm Wash solution (BD Pharmingen) and re-suspended in 1×BD Perm Wash solution (BD Pharmingen) containing 5 µg/ml of each of IL-2-FITC (BD Pharmingen), TNF-APC (BD Pharmingen) and IFN-γ-PeCy7 (BD Pharmingen) and incubated for 20 minutes at room temperature protected from light. Cells were washed with 1×BD Perm Wash solution (BD Pharmingen) and re-suspended in normal staining buffer and analyzed using a FC500 flow cytometer (Beckman Coulter).

Results

Humoral Immune Responses

Figure 1:
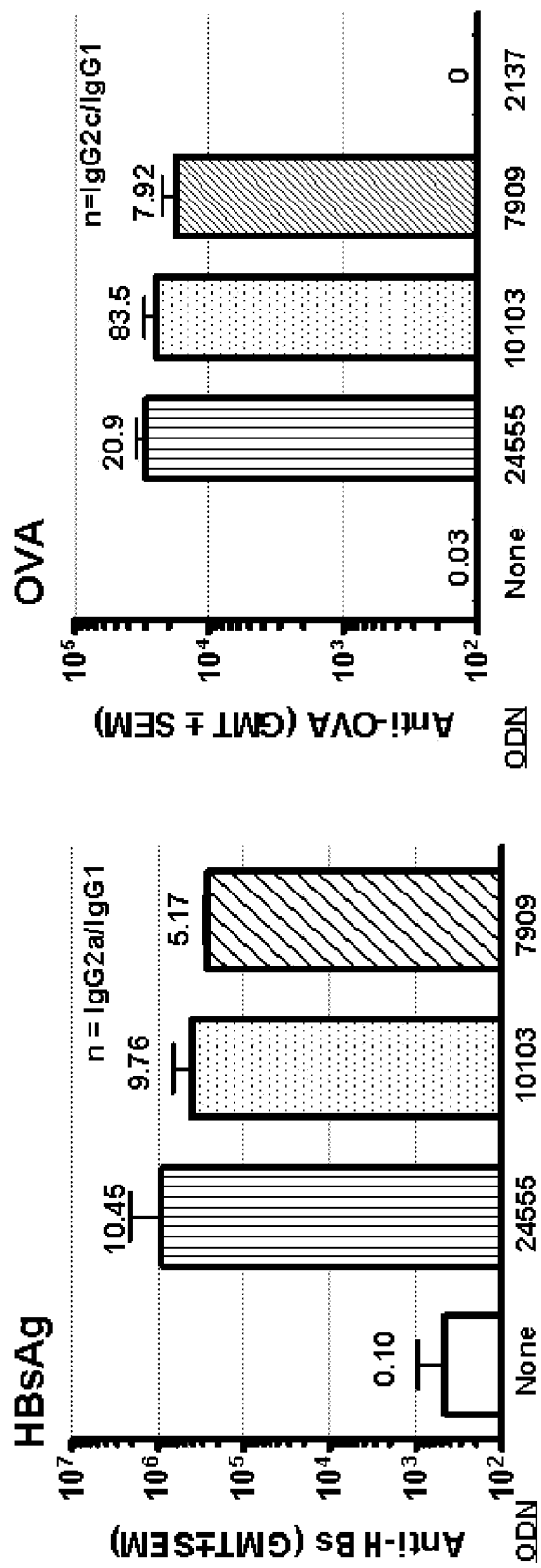
FIG. 1: Augmentation of humoral immune responses in mice. Adult (6-8 wk; n=10/gp) mice were immunized with 1 µg of HBsAg (left hand panel) or 20 µg OVA (right hand panel) without adjuvant or in combination with CPG 24555, 10103 or 7909 (10 µg) or non-CpG control ODN 2137 (10 µg.

All three CpG ODN tested (CPG 24555, 10103 and 7909) significantly enhanced HBsAg and OVA-specific total IgG titers in wild type mice (P<0.05). There was no significant difference amongst the three CpG ODN in terms of their ability to augment HBsAg or OVA specific total IgG in mice (FIG. 1).

The ability of CPG 24555, CPG 10103 and CPG 7909 to augment antibody titers in TLR9 deficient animals was tested using OVA. The overall antibody titers detected at 1 week post boost with any of the vaccination regimes was less than 100 and none of the CpG ODNs was able to significantly augment antibody titers against OVA compared to when vaccine was used alone or in combination with non-CpG ODN 2137 (data not shown).

In mice IgG isotype distribution is widely used as an indication of the nature of the immune response where high IgG2a or IgG2c levels are indicative of a Th1 biased immune response whereas high IgG1 titres are indicative of a Th2 biased immune response. All three CpG ODNs helped induce strong Th1 biased immune responses with IgG2a/IgG1 and IgG2c/IgG1 ratios>1 (FIG. 1) and with significantly enhanced IgG2a/c titers compared to when antigen was used alone (P<0.05) (FIG. 2).

Cellular Immune Responses: CTL Responses

A functional way to measure Th1-based responses is to measure CTL activity against antigen presenting target cells. As seen in FIG. 3, all CpG ODN tested were capable of significantly enhancing antigen-specific CTL responses against OVA in mice compared to when antigen was used alone or in combination with non-CPG ODN 2137 (P<0.05; FIG. 3 right panel). There was no significant difference between the CpG ODN tested in promoting the induction of OVA-specific CTL except at 6.25:1 E:T ratio where both CPG 24555 and CPG 7909 groups showed significantly higher OVA-specific CTL than groups receiving CPG 10103.

With HBsAg, both CPG 24555 and 10103 but not CPG 7909 were able to induce significantly higher antigen-specific CTL responses compared to when antigen was used alone. (P<0.05; FIG. 3 left panel). There was no significant difference between the CPG 24555 and CPG 10103 in their ability to promote the induction of HBsAg-specific CTL responses in mice.

CpG ODN mediated augmentation of CTL responses were not observed in TLR9 deficient mice (FIG. 4).

Antigen Specific CD8 T Cells

MHC Class I H-2 Kb-SIINFEKL specific tetramers were used to quantify CD8 T cell responses in mice immunized with OVA. All CpG ODN tested enhanced antigen-specific CD8 T cells compared to when OVA was used alone or in combination with the non-CpG control ODN 2137 (FIG. 5). CPG 7909 was superior to CPG 24555 and 10103 in promoting the induction of OVA-specific CD8 T cells (P<0.05). There was no significant difference between CPG 24555 and 10103 in their ability to induce OVA-specific CD8 T cells (P>0.05).

CPG mediated augmentation of OVA specific CD8 T cells was not observed in TLR9 deficient mice (FIG. 5).

Antigen Specific IFN-γ Secretion

Interferon gamma (IFN-γ) production in response to antigen stimulation as a measure of cellular immunity was also investigated by detection of the cytokine in culture supernatant of splenocytes re-stimulated with vaccinated antigen using enzyme immunoassay. Culture supernatants of splenocytes harvested from animals immunized with either HBsAg or OVA using CPG 24555 or CPG 10103 showed significantly higher levels of IFN-γ compared to ones immunized with antigen alone. When used with HBsAg, CPG 24555 was significantly better in promoting antigen specific IFN-γ secretion compared to CPG 10103 or CPG 7909 (FIG. 6; left panel). When used with OVA CPG 24555 was equal to CPG 10103 but superior to CPG 7909 in promoting antigen specific IFN-γ secretion (FIG. 6; right panel). CpG ODN mediated augmentation of antigen-specific IFN-γ secretion was not observed in TLR9 deficient animals (FIG. 7).

Antigen Specific Multi-Cytokine Secreting T Cell Populations

According to more recent findings, IFN-γ production by T cells alone is not predictive of the ability of antigen-specific T cells to induce protective immune response. Therefore, in this study we evaluated the ability of antigen-specific CD4 and CD8 T cells to produce IL-2, TNF-α and IFN-γ using polychromatic flow cytometry.

With both CD4 and CD8 T cells, a relatively low level of IL-2 secretion was seen in comparison to IFN-γ and TNF-α secretion (FIG. 8). With CD4 T cells, CPG 24555 helped induce higher percentage of double cytokine secreting T cells compared to CPG 10103 and 7909 (23% with CPG 24555 where as 4 and 6% with CPG 10103 and 7909 respectively). Overall, very low percentage of triple cytokine producing HBsAg specific CD4 T cells were observed (2, 0 and 1% with CPG 24555, 10103 and 7909 respectively) (FIG. 8A).

With CD8 T cells, both CPG 24555 and CPG 7909 helped induce high level of double cytokine secreting T cells compared to CPG 10103 (48 and 56% with CPG 24555 and CPG 7909 respectively, whereas only 19% with CPG 10103). Similar to CD4 cells, very low percentage of triple cytokine producing HBsAg-specific CD8+ T cells were observed (1, 0 and 0% with CPG 24555, 10103 and 7909 respectively) (FIG. 8B).

TABLE 1

Percentage of HBsAg-specific CD4+ T cells that are single, double or triple cytokine producers secreting IFN-γ and/or IL-2 and/or TNF-α

| CD4 + T cells | Ag alone | Ag + CpG 24555 | Ag + CpG 10103 |
|---|---|---|---|
| IFN-γ* | 69% | 53% | 36% |
| TNF-α* | 41% | 65% | 62% |
| IL-2* | 15% | 9% | 6% |
| IFN-γ/IL-2# | 7% | 2% | 0% |
| IFN-γ/TNF-α# | 10% | 22% | 2% |
| TNF-α/IL-2# | 8% | 5% | 2% |
| IFN-γ/IL-2/TNF-α | 0% | 2% | 0% |
| % of single cytokine producer | 75% | 75% | 96% |
| % producing at least two cytokines | 25% | 25% | 4% |

*indicates total proportion of cells producing these cytokines whether they are single, double or triple producers
indicates total proportion of cells producing these two cytokines whether they are double or triple producers

TABLE 2

Percentage of HBsAg-specific CD8+ T cells that are single, double or triple cytokine producers secreting IFN-γ and/or IL-2 and/or TNF-α

| CD8 + T cells | Ag alone | Ag + CpG 24555 | Ag + CpG 10103 |
|---|---|---|---|
| IFN-γ* | 63% | 67% | 76% |
| TNF-α* | 42% | 76% | 37% |
| IL-2* | 10% | 7% | 6% |
| IFN-γ/IL-2# | 5% | 2% | 0% |
| IFN-γ/TNF-α# | 10% | 47% | 18% |
| TNF-α/IL-2# | 2% | 2% | 1% |
| IFN-γ/IL-2/TNF-α | 2% | 1% | 0% |

TABLE 2-continued

Percentage of HBsAg-specific CD8+ T cells that are single, double or triple cytokine producers secreting IFN-γ and/or IL-2 and/or TNF-α

| CD8 + T cells | Ag alone | Ag + CpG 24555 | Ag + CpG 10103 |
|---|---|---|---|
| % of single cytokine producer | 87% | 51% | 81% |
| % producing at least two cytokines | 13% | 49% | 19% |

*indicates total proportion of cells producing these cytokines whether they are single, double or triple producers
indicates total proportion of cells producing these two cytokines whether they are double or triple producers Discussion Studies were designed to compare CPG 24555 with CPG 10103 and CPG 7909 for its ability to augment antigen-specific immune responses in mice when used with 2 model antigens: HBsAg and OVA. CPG 24555 and CPG 10103 have identical nucleotide sequence except CPG 24555 has a reversal of the 3' most CG dinucleotide resulting in the elimination of a CpG motif in CPG 24555. CPG 7909 is a B-class CpG ODN that has proven adjuvant activity in human clinical trials with a number of vaccine antigens.

Elimination of the 3' CpG motif in CPG 24555 did not have any negative impact on its ability to augment antigen-specific immune responses and showed equal (antibody responses and antigen-specific CD8 T cells as measured by tetramer staining) or better (antigen specific IFN-γ secretion) augmentation of adaptive immune responses compared to CPG 10103. Similarly CPG 24555 was equal to CPG 7909 in augmenting antigen specific antibody responses as well as CTL responses. CPG 24555 was superior to CPG 7909 in promoting antigen specific IFN-g secretion.

Augmentation of adaptive immune responses with all three CpG ODN tested were TLR9 dependent as no augmentation in adaptive immune responses were seen in TLR9 deficient mice.

As shown in table 1, a higher proportion of antigen-specific CD4+ T cells producing IFN-γ were obtained with CPG 24555. Also a higher proportion of poly-functional antigen-specific CD4+ T cells producing at least two cytokines among IFN-γ TNF-α and IL-2 (i.e., both IFN-γ and TNF-α, both IFN-γ and IL-2 or both TNF-α and IL-2, or even triple-producers secreting IFN-γ TNF-α and IL-2) was obtained.

As regard CD8+ T cells (table 2) a higher proportion of poly-functional antigen-specific CD8+ T cells producing two cytokines, and in particular IFN-γ and TNF-α, both IFN-γ and IL-2 was obtained.

Altogether, these results show that CPG 24555 is better than CPG 10103 for generating poly-functional antigen-specific T cells populations when used as an adjuvant. This can be of importance as poly-functional T cells, in particular in terms of chemokine production (such as IFN-γ, TNF-α and IL-2) are thought to be better effector cells compared to T cells that secrete a single cytokine.

Example 2

Comparison of CPG 24555 and CPG 10103

Nucleotide Sequences of ODNs Tested

CPG ODN 10103
(SEQ ID NO: 2)
5' T*C*G*T*C*G*T*T*T*T*T*C*G*G*T*C*G*T*T*T*T 3'

CPG ODN 24555
(SEQ ID NO: 1)
5' T*C*G*T*C*G*T*T*T*T*T*C*G*G*T*G*C*T*T*T*T 3'

Non-CpG ODN 22881
(SEQ ID NO: 4)
5' T*G*C*T*G*C*T*T*T*T*G*G*C*T*G*C*T*T*T*T 3'

Non-CpG ODN 2137
(SEQ ID NO: 5)
5' T*G*C*T*G*C*T*T*T*T*G*T*G*C*T*T*T*T*G*T*G*C*T*T 3'

*indicates phosphorothioate linkage (PS)

The underline portion of the sequences represents the difference between CPG ODN 10103 and CPG ODN 24555.

Optimal CpG motif for humans: GTCGTT

Innate Immunity in Human PBMC

Human PBMC (5×10⁶/ml) were incubated with varying concentrations of CPG 10103, CPG 24555 or non-CpG control ODN 22881 for 24 or 48 h. Cell supernatants were collected and assayed for cytokine/chemokine secretion using a commercial ELISA kit (FIG. 9A and FIG. 9B).

Innate Immunity In Vivo in BALB/c Mice

BALB/c mice (n=5/group) were injected subcutaneously with PBS (placebo control), CPG 24555, CPG 10103 or non-CpG control ODN 2137 at 100 µg dose level. Animals were bled at 3 hour post injection and plasma assayed for IP-10 (FIG. 10A) and IL-12 (FIG. 10B) or IL-6 (FIG. 10C) using commercial ELISA. Results shown are the group means±standard error of the mean (NS=not significant).

Humoral Immunity In Vivo in BALB/c Mice

BALB/c mice were injected intramuscularly with HBsAg (1 µg) with or without CPG 2455, CPG 10103 or non-CpG control ODN 2137 at 10 µg. The mice were injected on 0 and 14 days. Results shown are HBsAg specific total IgG titers at 2 weeks post boost measured by endpoint ELISA (FIG. 11A).

C57bl/6 mice were injected intramuscularly with OVA (20 µg) with or without CPG ODN 2455, CPG 10103 or non-CpG control ODN 2137 at 10 µg. The mice were injected on 0, 7 and 21 days. Results shown are OVA specific total IgG titers at 1 week post last boost (FIG. 11B).

BALB/c mice were injected intramuscularly with Influenza A HA from Texas 1/77, H3N2 (1 µg)±alum (25 µg Al3+) with or without CPG ODN 2455, CPG 10103 or non-CpG control ODN 2137 at 10 µg. Results shown are kinetics of HA specific total IgG at various times post immunization measured by end point ELISA (FIG. 11C).

T Cell Responses in BALB/c Mice

BALB/c mice were injected intramuscularly with HBsAg (1 µg) with or without CPG ODN 2455, CPG 10103 or non-CpG control ODN 2137 at 10 µg. The mice were injected on 0 and 14 days. Results shown are HBsAg specific CTL measured by $^{51}$Cr release at 2 weeks post boost (FIG. 12A).

C57bl/6 mice were injected intramuscularly with OVA (20 µg) with or without CPG ODN 2455, CPG 10103 or non-CpG control ODN 2137 at 10 µg. The mice were injected on 0, 7 and 21 days. Results shown are OVA specific CTL measured by $^{51}$Cr release at 1 week post last boost (FIG. 12B).

BALB/c mice were injected intramuscularly with HBsAg (1 µg) with or without CPG ODN 2455, CPG 10103 or non-CpG control ODN 2137 at 10 µg. The mice were injected on 0 and 14 days. Splenocytes from 2 week post last boost were incubated with respective antigen for 72 hours and culture supernatants tested for IFN-γ by ELISA (FIG. 13A).

C57bl/6 mice were injected intramuscularly with OVA (20 µg) with or without CPG ODN 2455, CPG 10103 or non-CpG control ODN 2137 at 10 µg. The mice were injected on 0, 7 and 21 days. Splenocytes from 1 week post last boost were incubated with respective antigen for 72 hours and culture supernatants tested for IFN-γ by ELISA (FIG. 13B).

Results and Discussion

CPG 10103 and CPG 24555 have identical nucleotide sequences except for the reversal of the 3' most CG dinucleotide present in CPG 10103 into GC in CPG 24555 resulting in elimination of a CpG motif in CPG 24555. Based on previous reports, given the same flanking sequence, motif location and spacing, an increased number of CPG motifs should lead to enhanced immune stimulation. Based on the prior knowledge, it was expected that CPG 24555 would be less immunostimulatory than CPG 10103 and less effective as a vaccine adjuvant. However, the results above demonstrate that CPG 24555 has similar or greater immunostimulatory potential and adjuvant activity compared to CPG 10103.

Example 3

Comparison of CPG 10103, CPG 24555 and CPG 7909 as a Vaccine Adjuvant to Influenza Hemagglutinin Antigen (HA) in BALB/C Mice Methods and Materials Female BALB/c mice (10/gp), were immunized by intramuscular (IM) injection into the left tibialis anterior (TA) muscle with Influenza A hemagglutinin (HA) from Texas 1/77, H3N2 (1 µg)±CpG or control ODN (10 mg)±alum (25 mg Al3+) in a total volume of 50 µl. Mice were bled at different time intervals post immunization to assess HA-specific antibody response. Half the animals per group were euthanized at 6 wks post immunization to assess cell mediated immune responses (CTL, HA-specific IFN-g secretion and flow cytometric analysis of T-cell cytokine secretion).

TABLE 3

| Reagent | Source, Lot N° | Stock Conc | Final Conc |
|---|---|---|---|
| Influenza A Antigen (Texas 1/77 H3N2) | Microbix Biosystems Inc. 13037A8 | 1.0 mg/ml | 0.02 mg/ml |
| Alum (Al3+) Alhydrogel "85" 2% | Cedarlane 85339 | 10.4 mg/ml | 0.5 mg/ml |
| CPG 7909 | Coley, Lot ACZ-03I-016-M | 37.15 mg/ml | 0.2 mg/ml |
| CPG 24555 (also known as CPG 10103_GC4) | Avecia, Lot#ASD-A0218-157 [labeled as CPG 10103] | 17.75 | 0.2 mg/ml |
| CPG 10103 | Dow Chemical, Lot# MM021230 | 24.51 mg/ml | 0.2 mg/ml |
| Control ODN 2137 | Coley, Lot# 008 | 22.18 mg/ml | 0.2 mg/ml |
| PBS | Sigma (P4244) Lot # 096K6064 | N/A | N/A |

Results and Discussion

Anti-HA at 6 Weeks Post Immunization

At 6 weeks post immunization, the amount of anti-HA was measured. CPG 24555 was superior to CPG 10103 and CPG 7909 in augmenting HA-specific IgG (FIG. 14).

Hemagglutination Inhibition (HIA) Titers at 4 Weeks Post Immunization

Figure 15:
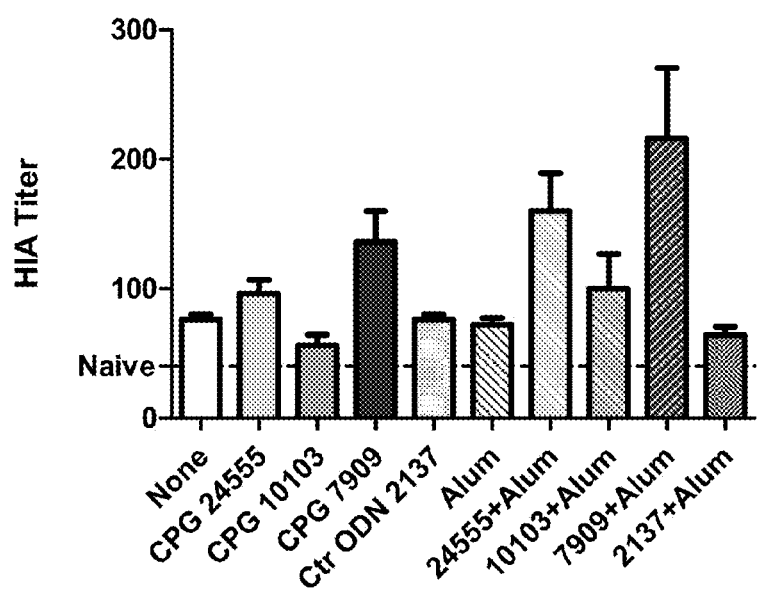

The functionality of the antibodies were evaluated using a hemagglutination inhibition assay (HIA). When used alone as adjuvant, CPG 24555 was superior to CPG 10103 (p=0.009) and equal to CPG 7909 (p=0.1) for augmenting HIA titers (FIG. 15). All 3 CpG ODN tested were equal for augmenting HIA titers when used in combination with alum.

HA-Specific IFNγ Secretion

The concentration of IFNγ secreted was measured. CPG 24555 when used alone as an adjuvant was superior to CPG 10103 for augmenting HA-specific IFN-γ secretion (marker of cell-mediated immunity) (FIG. 16). When used in combination with alum, CPG 24555 was superior to CPG 10103 and CPG 7909 for augmenting HA-specific IFN-γ secretion (FIG. 16).

Example 4

Comparison of CPG 24555 and CPG 7909 as a Vaccine Adjuvant to Hepatitis B Surface Antigen (HBsAg) in Cynomolgus Monkeys Materials and Methods Cynomolgus monkeys (3-5 yrs; 2.5 to 5.5 kg; n=5/gp; except for n=4 in HBsAg+IMX group) were immunized intramuscularly (0.6 ml IM injection in the right quadriceps) with:
1) Engerix-B (pediatric dose; 10 mg HBsAg)
2) Engerix-B+CPG 7909 (0.5 mg)
3) Engerix-B+CPG 24555 (0.5 mg)

Animals received 3 immunizations; at week 0 (prime), 4 (boost 1) and 8 (boost 2). The animals were bled pre-prime, 4 weeks post-prime (week 4), 2 weeks post-boost 1 (week 6), 4 weeks post-boost 1 (week 8) and 2 weeks post-boost 2 (week 10).

HBsAq Specific Immune Assays were Performed as Follows:
1) Antibody titer and avidity
2) Intracellular cytokine secretion (IL-2, IFN-γ, TNF-α)
3) Poly-functional T cells
4) ELISPOT assay: IL2, TNF-α, IFN-γ, Perforin Results and Discussion Humoral Responses A possibility of previous exposure of animals in this study to hepatitis B virus was evident by high level of HBsAg specific antibody titers detected at pre vaccination. Furthermore, one animal in the shipment tested positive for HBV by serology suggesting possible exposure to HBV. However, all animals used in this study tested negative for HBV by PCR. There was an increase in anti-HBsAg titer with each boost. The addition of CpG to Engerix-B enhanced HBsAg specific antibody titers compared to when Engerix-B was used alone (FIG. 17). Furthermore, addition of CpG enhanced antibody avidity compared to when Engerix-B was used alone (FIG. 18). CPG 24555 was equal to CPG 7909 in enhancing both antibody titer and avidity.

T Cell Responses: Intracellular Cytokine Secretion by CD4 T Cells

The addition of CpG to Engerix-B tended to increase the frequency of CD4 T cell mediated IFN-γ and TNF-α but not IL-2 secretion (FIGS. 19A, B and C). Overall, CPG 24555 was equal to or better than CPG 7909 for the induction of CD4 mediated cytokines.

T Cell Responses: Poly Functional CD4 T Cells; Quantitative Analysis

The number of cells secreting one, two or three cytokines was measured at week 10 (2 weeks post-boost 2). CPG 24555 was equal to CPG 7909 in inducing Engerix-B specific CD4 T cell secreting one cytokine. Overall, relatively low level of triple cytokine producing CD4 T cells were detected. However, CPG 24555 induced higher triple cytokine producing CD4 T cells than CPG 7909 or Engerix-B alone (FIG. 20A). Furthermore, animals immunized with Engerix-B+ CPG 24555 had a higher proportion of triple cytokine producing T cells compared to animals immunized with Engerix-B alone or Engerix-B+CPG 7909 (FIG. 20B).

T Cell Responses: Poly Functional CD4 T Cells; Qualitative Analysis

Figure 21A:
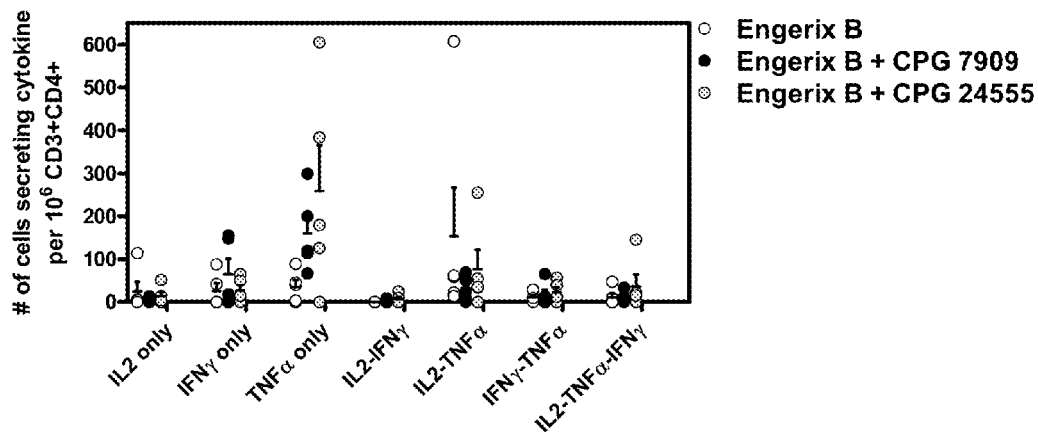
Figure 21B:
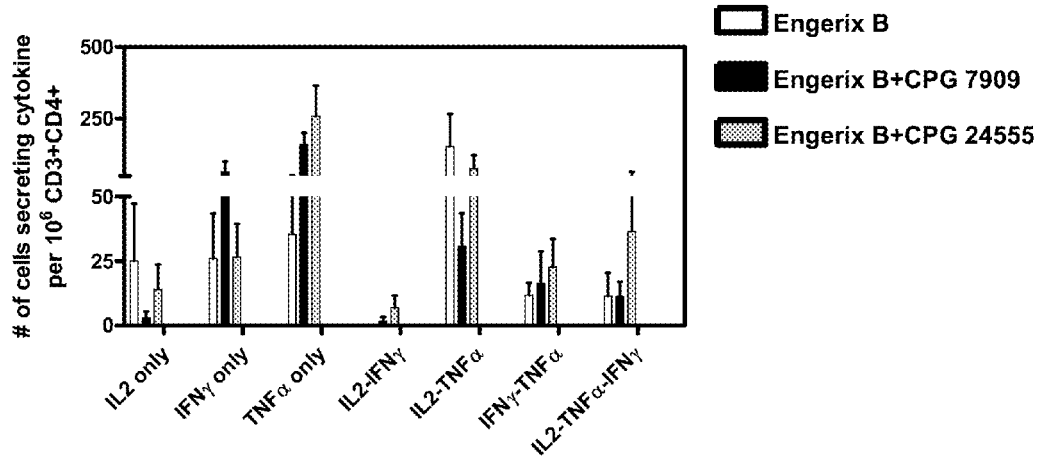

The number of cells secreting IL-2, IFN-γ and TNFα, or combinations of these cytokines, was measured. CPG 24555 was equal to or better than CPG 7909 for inducing poly-functional T cells (FIG. 21A and FIG. 21B).

T Cell Responses: Poly Functionality of CD4 T cells

The proportion of triple cytokine producing CD4 T cells was measured at 2 weeks post boost 2. A higher proportion of triple cytokine producing CD4 T cells was observed with CPG 24555 than with CPG 7909.

CONCLUSIONS

Based on the data, elimination of the 3' CpG motif in CPG 24555 did not have any negative impact on its ability to augment antigen-specific immune responses and showed equal or better augmentation of adaptive immune responses compared to CPG 10103 and CPG 7909. Adjuvant activity of CPG 24555 seen with multiple antigens in mice was also translated into non human primates with CPG 24555 showing equal (humoral immunity) or superior (Ag-specific poly functional T cells) adjuvant activity to CPG 7909 with hepatitis B surface antigen in cynomolgus monkeys.

Those skilled in the art will recognize, or be able to ascertain using no more than routine experimentation, many equivalents of the specific embodiments of the invention described herein. Such equivalents are intended to be encompassed by the following claims.

---

We claim:

1. An immunostimulatory oligonucleotide comprising the nucleotide sequence

5' TCGTCGTTTTTCGGTGCTTTT 3'.    (SEQ ID NO: 1)

2. The immunostimulatory oligonucleotide of claim 1, wherein the oligonucleotide comprises one or more modified linkages.

3. The immunostimulatory oligonucleotide of claim 2, wherein the oligonucleotide comprises one or more phosphorothioate linkages.

4. The immunostimulatory oligonucleotide of claim 1, wherein the oligonucleotide comprises at least one lipophilic substituted nucleotide analog and a pyrimidine-purine dinucleotide.

* * * * *